(12) United States Patent
Van Bladel et al.

(10) Patent No.: US 11,478,353 B2
(45) Date of Patent: Oct. 25, 2022

(54) PERCUTANEOUS ARTERIAL ACCESS TO POSITION TRANS-MYOCARDIAL IMPLANT DEVICES AND METHODS

(71) Applicant: BioVentrix, Inc., San Ramon, CA (US)

(72) Inventors: Kevin Van Bladel, Livermore, CA (US); Serjan Nikolic, San Francisco, CA (US); Lon Annest, New York, NY (US); Rovil Arcia, Fremont, CA (US)

(73) Assignee: BioVentrix, Inc., San Ramon, CA (US)

( * ) Notice: Subject to any disclaimer, the term of this patent is extended or adjusted under 35 U.S.C. 154(b) by 284 days.

(21) Appl. No.: 15/418,152

(22) Filed: Jan. 27, 2017

(65) Prior Publication Data

US 2017/0216032 A1    Aug. 3, 2017

Related U.S. Application Data

(60) Provisional application No. 62/288,978, filed on Jan. 29, 2016.

(51) Int. Cl.
*A61F 2/24* (2006.01)
*A61B 17/04* (2006.01)
*A61B 17/00* (2006.01)

(52) U.S. Cl.
CPC ........ *A61F 2/2481* (2013.01); *A61B 17/0401* (2013.01); *A61F 2/2487* (2013.01);
(Continued)

(58) Field of Classification Search
CPC .... A61F 2/2478; A61F 2/2481; A61F 2/2487; A61F 2002/2484; A61F 2002/249;
(Continued)

(56) References Cited

U.S. PATENT DOCUMENTS 4,007,743 A    2/1977  Blake
5,154,709 A   10/1992  Johnson
(Continued)

FOREIGN PATENT DOCUMENTS

EP    1 078 644 A1    2/2001
WO    00/06028 A1     2/2000
(Continued)

OTHER PUBLICATIONS

European Examination Report of EP Patent Application 05810316.9 dated Mar. 10, 2009, 6 pages.
(Continued)

*Primary Examiner* — Elizabeth Houston
*Assistant Examiner* — Lindsey Bachman
(74) *Attorney, Agent, or Firm* — Nixon & Vanderhye P.C.

(57) ABSTRACT

A system for treating a heart includes a catheter that is advanceable into a chamber of the heart and that is repositionable within the chamber between a septal wall and an external wall to enable penetration of the septal and external walls via a needle that is disposed within a lumen of the catheter. A first guidewire is deliverable through the penetration of the septal wall so that a distal end of the first guidewire is disposed within another chamber of the heart. A second guidewire is deliverable through the penetration of the external wall so that a distal end of the second guidewire is disposed externally of the external wall. The first guidewire is connectable to the second guidewire to join or form a path within the chamber that extends between the septal wall and the external wall.

19 Claims, 23 Drawing Sheets

(52) U.S. Cl.
CPC .............. *A61B 2017/00243* (2013.01); *A61B 2017/00575* (2013.01); *A61B 2017/00632* (2013.01); *A61B 2017/00783* (2013.01); *A61B 2017/0419* (2013.01); *A61B 2017/0464* (2013.01)

(58) Field of Classification Search
CPC . A61B 17/0057; A61B 17/34; A61B 17/3468; A61B 2017/00243
See application file for complete search history.

(56) References Cited

U.S. PATENT DOCUMENTS

| | | | |
|---|---|---|---|
| 5,295,958 A | 3/1994 | Shturman | |
| 5,336,252 A | 8/1994 | Cohen | |
| 5,482,037 A | 1/1996 | Borghi | |
| 5,755,697 A | 5/1998 | Jones et al. | |
| 5,810,884 A | 9/1998 | Kim | |
| 5,830,224 A | 11/1998 | Cohn et al. | |
| 5,865,730 A | 2/1999 | Fox et al. | |
| 5,868,770 A | 2/1999 | Rygaard | |
| 5,961,440 A | 10/1999 | Schweich, Jr. et al. | |
| 6,010,476 A | 1/2000 | Saadat | |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,059,719 A | 5/2000 | Yamamoto | |
| 6,080,182 A | 6/2000 | Shaw et al. | |
| 6,125,852 A | 10/2000 | Stevens et al. | |
| 6,155,968 A | 12/2000 | Wilk | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,166,684 A | 12/2000 | Yoshikawa et al. | |
| 6,258,021 B1 | 7/2001 | Wilk | |
| 6,260,552 B1* | 7/2001 | Mortier ............ A61B 17/00234 128/898 | |
| 6,406,420 B1 | 6/2002 | McCarthy et al. | |
| 6,478,029 B1 | 11/2002 | Boyd et al. | |
| 6,494,211 B1 | 12/2002 | Boyd et al. | |
| 6,494,825 B1 | 12/2002 | Talpade | |
| 6,511,416 B1 | 1/2003 | Green et al. | |
| 6,572,529 B2 | 6/2003 | Wilk | |
| 6,616,684 B1* | 9/2003 | Vidlund ............ A61B 17/00234 606/213 | |
| 6,623,508 B2 | 9/2003 | Shaw et al. | |
| 6,705,988 B2 | 3/2004 | Spence et al. | |
| 6,709,382 B1 | 3/2004 | Horner | |
| 6,723,038 B1 | 4/2004 | Schroeder et al. | |
| 6,746,471 B2 | 6/2004 | Mortier et al. | |
| 6,776,754 B1* | 8/2004 | Wilk ................ A61B 17/00234 128/898 | |
| 6,808,488 B2 | 10/2004 | Mortier | |
| 6,859,662 B2 | 2/2005 | Bombardini | |
| 6,890,295 B2 | 5/2005 | Michels et al. | |
| 7,146,225 B2 | 12/2006 | Guenst et al. | |
| 7,326,177 B2 | 2/2008 | Williamson | |
| 7,373,207 B2 | 5/2008 | Lattouf | |
| 7,390,329 B2 | 6/2008 | Westra et al. | |
| 7,431,691 B1 | 10/2008 | Wilk | |
| 7,507,200 B2 | 3/2009 | Okada | |
| 7,637,924 B2 | 12/2009 | Gifford et al. | |
| 7,722,523 B2 | 5/2010 | Mortier et al. | |
| 7,753,923 B2 | 7/2010 | St. Goar et al. | |
| 7,766,816 B2 | 8/2010 | Chin et al. | |
| 7,785,248 B2 | 8/2010 | Annest et al. | |
| 7,842,015 B2 | 11/2010 | Chachques et al. | |
| 7,942,854 B1 | 5/2011 | Von Oepen et al. | |
| 8,066,766 B2 | 11/2011 | To et al. | |
| 8,123,668 B2 | 2/2012 | Annest et al. | |
| 8,268,009 B2 | 9/2012 | Teitelbaum et al. | |
| 8,382,829 B1* | 2/2013 | Call ..................... A61F 2/2487 623/2.37 | |
| 8,394,008 B2 | 3/2013 | Annest et al. | |
| 8,425,402 B2 | 4/2013 | Annest et al. | |
| 8,449,442 B2 | 5/2013 | Annest et al. | |
| 8,491,455 B2 | 7/2013 | Annest et al. | |
| 8,506,474 B2 | 8/2013 | Chin et al. | |
| 8,636,639 B2 | 1/2014 | Annest et al. | |
| 8,968,175 B2 | 3/2015 | Annest et al. | |
| 8,979,750 B2 | 3/2015 | Bladel et al. | |
| 8,986,189 B2 | 3/2015 | Chin et al. | |
| 9,039,594 B2 | 5/2015 | Annest et al. | |
| 9,044,231 B2 | 6/2015 | Annest et al. | |
| 9,095,363 B2 | 8/2015 | Bladel et al. | |
| 9,119,720 B2 | 9/2015 | Chin et al. | |
| 9,173,711 B2 | 11/2015 | Butler et al. | |
| 9,173,712 B2 | 11/2015 | Annest et al. | |
| 9,211,115 B2 | 12/2015 | Annest et al. | |
| 9,259,319 B2 | 2/2016 | Chin et al. | |
| 9,402,722 B2 | 8/2016 | Annest et al. | |
| 9,486,206 B2 | 11/2016 | Annest et al. | |
| 9,526,618 B2 | 12/2016 | Chin et al. | |
| 2001/0025171 A1 | 9/2001 | Mortier et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0077655 A1 | 6/2002 | Frova | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2002/0198563 A1 | 12/2002 | Gainor et al. | |
| 2003/0032979 A1 | 2/2003 | Mortier et al. | |
| 2003/0163165 A1 | 8/2003 | Bornzin et al. | |
| 2003/0166992 A1 | 9/2003 | Schweich, Jr. et al. | |
| 2003/0181928 A1 | 9/2003 | Vidlund et al. | |
| 2003/0181951 A1 | 9/2003 | Cates | |
| 2003/0220587 A1 | 11/2003 | Swenson | |
| 2003/0233022 A1 | 12/2003 | Vidlund et al. | |
| 2004/0064143 A1 | 4/2004 | Hicken et al. | |
| 2004/0082837 A1 | 4/2004 | Willis | |
| 2004/0088035 A1 | 5/2004 | Guenst et al. | |
| 2004/0138526 A1 | 7/2004 | Guenst | |
| 2004/0158123 A1 | 8/2004 | Jayaraman | |
| 2004/0167374 A1 | 8/2004 | Schweich | |
| 2004/0167580 A1 | 8/2004 | Mann et al. | |
| 2004/0225304 A1 | 11/2004 | Vidlund et al. | |
| 2004/0267306 A1 | 12/2004 | Blaeser et al. | |
| 2005/0065506 A1 | 3/2005 | Phan | |
| 2005/0075723 A1 | 4/2005 | Schroeder et al. | |
| 2005/0096498 A1 | 5/2005 | Houser et al. | |
| 2005/0137688 A1 | 6/2005 | Salahieh et al. | |
| 2005/0143620 A1 | 6/2005 | Mortier et al. | |
| 2005/0149115 A1 | 7/2005 | Roue et al. | |
| 2005/0177180 A1* | 8/2005 | Kaganov ............... A61F 2/2445 606/151 |
| 2005/0192599 A1 | 9/2005 | Demarais | |
| 2005/0215851 A1 | 9/2005 | Kim et al. | |
| 2005/0288613 A1 | 12/2005 | Heil, Jr. | |
| 2006/0004408 A1 | 1/2006 | Morris et al. | |
| 2006/0079736 A1 | 4/2006 | Chin et al. | |
| 2006/0135962 A1 | 6/2006 | Kick et al. | |
| 2006/0131238 A1 | 7/2006 | Hall | |
| 2006/0161040 A1 | 7/2006 | McCarthy et al. | |
| 2006/0161238 A1 | 7/2006 | Hall | |
| 2006/0167416 A1 | 7/2006 | Mathis et al. | |
| 2006/0178550 A1 | 8/2006 | Jenson | |
| 2006/0200002 A1 | 9/2006 | Guenst | |
| 2006/0241340 A1 | 10/2006 | Schroeder et al. | |
| 2006/0247672 A1 | 11/2006 | Vidlund et al. | |
| 2006/0276684 A1 | 12/2006 | Speziali | |
| 2007/0005018 A1 | 1/2007 | Tkebuchava | |
| 2007/0010876 A1 | 1/2007 | Salahieh et al. | |
| 2007/0049971 A1 | 3/2007 | Chin et al. | |
| 2007/0055303 A1 | 3/2007 | Vidlund et al. | |
| 2007/0073274 A1 | 3/2007 | Chin et al. | |
| 2007/0112244 A1 | 5/2007 | McCarthy et al. | |
| 2007/0161846 A1 | 7/2007 | Nikotic et al. | |
| 2007/0203503 A1 | 8/2007 | Salahieh et al. | |
| 2007/0265658 A1 | 11/2007 | Nelson et al. | |
| 2007/0287884 A1 | 12/2007 | Schena | |

(56) References Cited

U.S. PATENT DOCUMENTS

| | | | |
|---|---|---|---|
| 2008/0058650 A1 | 3/2008 | Saadat et al. | |
| 2008/0082132 A1 | 4/2008 | Annest et al. | |
| 2008/0097148 A1 | 4/2008 | Chin et al. | |
| 2008/0234717 A1 | 9/2008 | Bruszewski | |
| 2008/0269551 A1 | 10/2008 | Annest et al. | |
| 2008/0294251 A1* | 11/2008 | Annest | A61B 17/0401 623/3.1 |
| 2009/0093670 A1 | 4/2009 | Annest et al. | |
| 2009/0270980 A1 | 10/2009 | Schroeder et al. | |
| 2009/0287165 A1 | 11/2009 | Drapeau et al. | |
| 2009/0287304 A1 | 11/2009 | Dahlgren et al. | |
| 2010/0010538 A1 | 1/2010 | Juravic et al. | |
| 2010/0016655 A1 | 1/2010 | Annest et al. | |
| 2010/0030142 A1 | 2/2010 | Onishi | |
| 2010/0057000 A1 | 3/2010 | Melsheimer et al. | |
| 2010/0268020 A1 | 10/2010 | Chin et al. | |
| 2011/0160750 A1 | 6/2011 | Annest et al. | |
| 2011/0270191 A1 | 11/2011 | Paul et al. | |
| 2011/0301622 A1 | 12/2011 | Oren | |
| 2012/0190958 A1 | 7/2012 | Annest et al. | |
| 2012/0239003 A1 | 9/2012 | Julson et al. | |
| 2013/0030522 A1* | 1/2013 | Rowe | A61B 17/0401 623/2.36 |
| 2013/0090523 A1 | 4/2013 | Van Bladel et al. | |
| 2013/0090672 A1 | 4/2013 | Butler et al. | |
| 2013/0090684 A1 | 4/2013 | Van Bladel et al. | |
| 2013/0096579 A1 | 4/2013 | Annest et al. | |
| 2013/0324787 A1 | 12/2013 | Chin et al. | |
| 2013/0325041 A1 | 12/2013 | Annest et al. | |
| 2014/0031613 A1 | 1/2014 | Annest et al. | |
| 2014/0051916 A1 | 2/2014 | Chin et al. | |
| 2014/0207174 A1* | 7/2014 | Hackett | A61F 2/01 606/200 |
| 2014/0330296 A1 | 11/2014 | Annest et al. | |
| 2014/0350417 A1 | 11/2014 | Bladel et al. | |
| 2014/0371789 A1* | 12/2014 | Hariton | A61F 2/2427 606/215 |
| 2015/0066082 A1 | 3/2015 | Moshe et al. | |
| 2015/0066139 A1 | 3/2015 | Bladel et al. | |
| 2015/0238182 A1 | 8/2015 | Annest et al. | |
| 2016/0022422 A1 | 1/2016 | Annest et al. | |
| 2016/0030026 A1 | 2/2016 | Bladel et al. | |
| 2016/0089132 A1 | 3/2016 | Butler et al. | |
| 2016/0095600 A1 | 4/2016 | Annest et al. | |
| 2016/0120648 A1 | 5/2016 | Chin et al. | |
| 2016/0206427 A1 | 7/2016 | Annest et al. | |
| 2016/0262891 A1 | 9/2016 | Chin et al. | |
| 2016/0338835 A1 | 11/2016 | Bladel et al. | |

FOREIGN PATENT DOCUMENTS

| | | |
|---|---|---|
| WO | 2002/30335 A2 | 4/2002 |
| WO | 2003/032818 A3 | 4/2003 |
| WO | 2004-043267 A2 | 5/2004 |
| WO | 2005/092203 A1 | 10/2005 |
| WO | 2006/044467 A2 | 4/2006 |
| WO | 2006086434 A1 | 8/2006 |
| WO | 2007/022519 A2 | 2/2007 |
| WO | 2007-100409 A2 | 9/2007 |
| WO | 2013-049761 A1 | 4/2013 |

OTHER PUBLICATIONS

Extended European Examination Report of EP Patent Application 06802038.7 dated Nov. 12, 2013, 13 pages.
Office Action of EP Patent Application 06802038.7 dated Sep. 11, 2014, 4 pages.
International Report on Patentability of PCT/US2012/058074 dated Apr. 10, 2014, 8 pages.
International Report on Patentability of PCT/US2012/058176 dated Apr. 10, 2014, 11 npages.
International Search Report and Written Opinion of PCT Application No. PCT/US06/22594, dated Oct. 1, 2008, 4 pages.
International Search Report and Written Opinion of PCT Application No. PCT/US06/32663, dated Jul. 31, 2007, 5 pages.
International Search Report and Written Opinion of PCT Application No. PCT/US08/64255, dated Sep. 29, 2008, 13 pages.
International Search Report and Written Opinion of PCT Application No. PCT/US08/78810, dated Feb. 12, 2009,9 pages.
International Search Report and Written Opinion of PCT Application No. PCT/US09/51288, dated Sep. 15, 2009, 7 pages.
International Search Report and Written Opinion of PCT Application No. PCT/US12/58074, dated Mar. 13, 2013, 18 pages.
International Search Report and Written Opinion of PCT Application No. PCT/US2005/036690, dated Jul. 9, 2007, 6 pages.
International Search Report and Written Opinion of PCT/US2012/058106, dated Nov. 26, 2012, 14 pages.
International Search Report and Written Opinion of PCT/US2012/58176, dated Jan. 8, 2013, 19 pages.
International Search Report and Written Opinion of PCT/US2012/058182, dated Mar. 1, 2013, 12 pages.
USPTO—STIC Search Results—NPL (Dec. 11, 2014).
USPTO—STIC Search Results—Patents (Dec. 11, 2014).
International Search Report and Written Opinion of PCT Application No. PCT/US2014/053209 dated Mar. 2, 2015, 18 pages.
International Search Report and Written Opinion of PCT Application No. PCT/US2014/038834 dated Oct. 16, 2014, 16 pages.
International Report on Patentability of PCT Application No. PCT/US2014/038834 dated Dec. 3, 2015, 11 pages.
European Examination Report of EP Patent Application 12837466.7 dated Jun. 6, 2016, 14 pages.

* cited by examiner

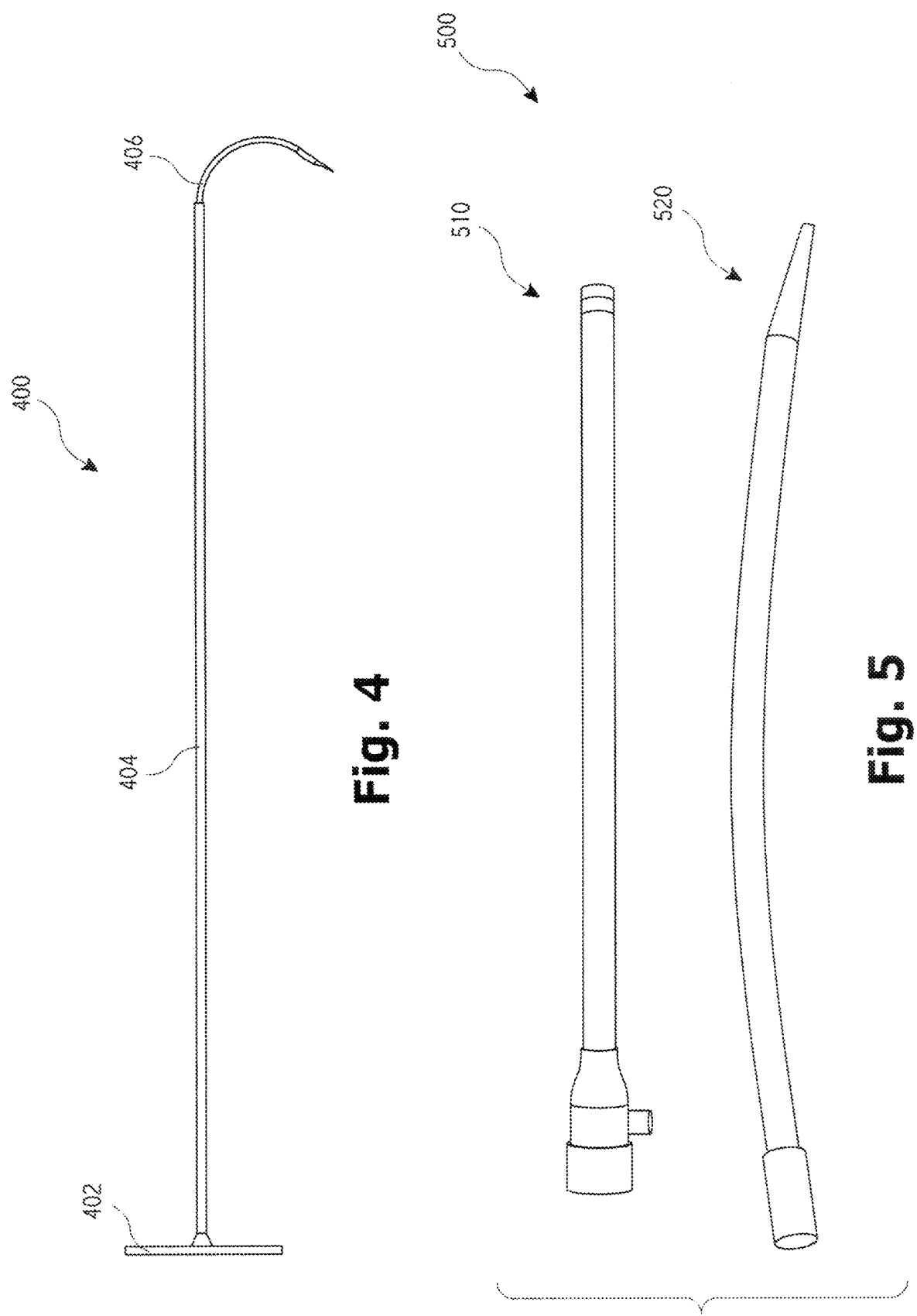

PERCUTANEOUS ARTERIAL ACCESS TO POSITION TRANS-MYOCARDIAL IMPLANT DEVICES AND METHODS

CROSS-REFERENCE TO RELATED APPLICATIONS

This application claims priority to U.S. patent application Ser. No. 62/288,978 filed Jan. 29, 2016, entitled "Percutaneous Arterial Access to Position Trans-Myocardial Implant Devices and Methods for Treatment of Congestive Heart Failure and Other Conditions," the entire disclosure of which is hereby incorporated by reference, for all purposes, as if fully set forth herein.

BACKGROUND

Heart implants are currently used to resize or alter the geometry of a ventricle in a failing heart, such as by reducing its radius of curvature through the process of excluding a portion of the circumference from contact with blood, and thereby reduce wall stress on the heart and improve the heart's pumping performance. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF DESCRIPTION

The embodiments described herein are particularly useful for positioning anchors or heart implants against heart walls. According to one aspect, a system for treating a heart within a patient is provided herein. The heart has first and second chambers with a septum there between and the second chamber has an external wall. The system includes an elongate shaft that has a proximal end and a distal end with a lumen extending there between. The distal end of the elongate shaft is configured to be advanced along a first path from outside the patient and through the vasculature into the second chamber of the heart so that the distal end of the elongate shaft is positioned within the second chamber. The elongate shaft is steerable so that the distal end of the elongate shaft is repositionable within the second chamber between the septum and the external wall to enable penetration of the septum and external wall.

A first guidewire is deliverable through the lumen of the elongate shaft and through the septum when the distal end of the elongate shaft is positioned adjacent the septum. The first guidewire is deliverable through the septum so that a distal end of the first guidewire is positioned within the first chamber. The first guidewire may be used to penetrate the septum, or a needle may be used to penetrate the septum and the first guidewire may be inserted through the penetration made by the needle. A second guidewire is deliverable through the lumen of the elongate shaft and through the external wall when the distal end of the elongate shaft is positioned adjacent the external wall. The second guidewire is deliverable through the external wall so that a distal end of the second guidewire is positioned externally of the external wall. The second guidewire may be used to penetrate the external wall, or a needle may be used to penetrate the external wall and the second guidewire may be inserted through the penetration made by the needle. The first guidewire is coupleable to the second guidewire to join a path within the second chamber that extends between the septum and the external wall.

The system may further include a needle is disposed within the lumen of the elongate shaft. The needle may be deliverable from the within the lumen of the elongate shaft in order to penetrate the septum and to penetrate the external wall when the distal end of the elongate shaft is positioned adjacent the septum and external wall respectively. The system may also include an additional elongate shaft that has a proximal end and a distal end. The distal end of the additional elongate shaft may be configured to be advanced along a second path from outside the heart and through the vasculature into the first chamber of the heart so that the distal end of the additional elongate shaft is disposed in the first chamber. A flexible body may be slidably coupled to the additional elongate shaft. The flexible body may have a distal end portion that is configured for in situ coupling, within the first chamber of the heart, with the distal end of the first guidewire. Coupling of the first guidewire and the distal end portion of the flexible body may be done to join a path of the first guidewire with the second path of the additional elongate shaft body. In a specific embodiment, the flexible body is a snare device that is slidably disposed within a lumen of the additional elongate shaft and that is axially advanceable therefrom. The snare device may have an opening that is configured for capturing the first guidewire within the first chamber. The snare device may be biased to expand from a low profile configuration when released in the first chamber in order to expand the opening.

The system further includes an implant that is configured to be advanced along the joined path of the first guidewire and the second guidewire. The implant includes a first anchor that is advanceable along the joined path and into position against the septum within the first chamber. The implant also includes a second anchor that is advanceable along the joined path and into position against the external wall. The implant further includes an elongate tension member having a first end that is coupled with the first anchor and a second end that is coupleable with the second anchor. The tension member is configured to extend from the first anchor in the first chamber, through the septum, through the second chamber, and through the external wall such that applying tension between the first and second anchors with the tension member urges the septum and the external wall to engage.

The system may further include an external elongate shaft having a proximal end and a distal end. The distal end of the external elongate shaft may be configured to be advanced from outside the patient to the external wall of the second chamber so that the distal end of the external elongate shaft is disposed adjacent the external wall. The external elongate shaft may be further configured for coupling with the second guidewire for extracting the second guidewire from the external wall to outside the patient body. The external elongate shaft may include a second snare device that is slidably disposed within a lumen of the external elongate shaft and that is axially extendable therefrom. The second snare device may be positionable on the external wall of the second chamber for coupling with the second guidewire.

The system may additionally include a coupling member that is fixedly securable to a proximal end of the first guidewire and to a proximal end of the second guidewire to couple the first guidewire to the second guidewire. In other embodiments, the first guidewire may be a first end of a single elongate guidewire and the second guidewire may be a second end of the single elongate guidewire so that the first and second guidewires are opposing ends of the same guidewire.

The system may additionally include an apical anchor device. The apical anchor device may include an elongate tension member, an anchor that is attached to a proximal end of the elongate tension member, and a needle that is attached to a distal end of the elongate tension member. The needle may have a tissue penetrating tip that is configured for penetrating through external walls of an apex of the heart. The elongate tension member may couple the needle and the anchor. The elongate tension member may also be configured to be tensioned after the needle penetrates through the external walls of the apex so as to advance the anchor into engagement with one of the external walls of the apex. The needle typically has a curved or arcuate configuration and is made of a more rigid material than the elongate tension member. The anchor of the apical anchor device is axially affixed and pivotably coupled to the elongate tension member so that the anchor is able to pivot from a low-profile configuration to a deployed configuration.

The system may additionally include an alignment device for aligning the first anchor within the first chamber. The alignment device typically includes an elongate body having a proximal end and a distal end with a lumen extending there between. The alignment device also includes an opening in the distal end of the elongate body that is configured so that the first anchor is positionable within the opening. The alignment device includes a reposition mechanism that is releasably coupled with the first anchor and that is operationally coupled with the elongate body so that a first operation of the reposition mechanism causes the first anchor to be retractably deployed from the opening of the elongate body. The reposition mechanism includes a guidewire or cable that is slidably disposed within the lumen of the elongate body and within an axial lumen of the first anchor. The elongate body is configured so that distal sliding of the guidewire or cable within the lumen of the elongate body causes a portion of the guidewire or cable to protrude outwardly from the opening of the elongate body thereby causing the first anchor to be retractably deployed from the opening.

The system may additionally include an axial force-application tool that is configured for applying a desired anchor migration inhibiting force between the first and second anchors. The axial force-application tool is further configured to adjust the second anchor between a variable force mode in which axial sliding of the second anchor along the tension member is enabled and a set-force mode in which axial sliding of the second anchor is inhibited.

According to another aspect, a system for treating a heart within a patient is provided herein. The heart has first and second chambers with a septum there between and the second chamber has an external wall. The system includes a first elongate shaft having a proximal end and a distal end. The distal end of the first elongate shaft is configured to be advanced from outside the patient and through the vasculature into the first chamber of the heart so that the distal end of the first elongate shaft is disposed in the first chamber.

The system also includes a second elongate shaft having a proximal end and a distal end. The distal end of the second elongate shaft is configured to be advanced from outside the heart and through the vasculature into the second chamber of the heart so that the distal end of the second elongate shaft is disposed in the second chamber. The system additionally includes a first guidewire that is deliverable from within a lumen of the second elongate shaft and through the septum so that a distal end of the first guidewire is disposed in the first chamber. The system additionally includes a flexible body that is slidably coupled to the first elongate shaft. The flexible body has a distal end portion that is configured for in situ coupling, within the first chamber of the heart, with the distal end of the first guidewire such that the first guidewire is extractable from the first chamber via the first elongate shaft. The system additionally includes a second guidewire that is deliverable from within the lumen of the second elongate shaft and through the external wall so that a distal end of the second guidewire is disposed external to the external wall. The second guidewire is extractable from the external wall to outside the patient body. The second guidewire is coupled to the first guidewire to form a path that extends from outside the patient body at a first location, into the first chamber, through the septum, through the second chamber, through the external wall, and outside the patient body at a second location.

In some embodiments, the system additionally includes a tissue penetrating member that is operably coupled with the second elongate shaft. The tissue penetrating member is configured to penetrate the septum when the distal end of the second elongate shaft is positioned adjacent the septum and is configured to penetrate the external wall when the distal end of the second elongate shaft is positioned adjacent the external wall. Alternatively, the system may not include a tissue penetrating member and the first guidewire may be used to penetrate through the septum and the second guidewire may be used to penetrate through the external wall.

In some embodiments, the system additionally includes an implant that is configured to be advanced along the formed path. The implant includes a first anchor that is advanceable along the formed path and into position against the septum. The implant also includes a second anchor that is advanceable along the formed path and into position against the external wall. The implant further includes an elongate tension member having a first end that is coupled with the first anchor and a second end that is coupleable with the second anchor. The tension member is configured to extend from the first anchor in the first chamber, through the septum, through the second chamber, and through the external wall such that applying tension between the first and second anchors with the tension member urges the septum and the external wall to engage.

In some embodiments, the system may additionally include a coupling member that is fixedly securable to a proximal end of the first guidewire and to a proximal end of the second guidewire to couple the first guidewire to the second guidewire. In other embodiments, the first guidewire is a first end of a single elongate guidewire and the second guidewire is a second end of the single elongate guidewire so that the first and second guidewires are opposing ends of the same guidewire.

According to another aspect, a method for treating a heart within a patient is provided herein. The heart has first and second chambers with a septum there between and the second chamber has an exterior wall. The method includes advancing an elongate shaft from outside the patient and through the vasculature so that a distal end of the elongate shaft is disposed in the second chamber. The elongate shaft has a proximal end and a lumen that extends between the proximal end and the distal end. The method also includes positioning the distal end of the elongate shaft adjacent the septum and penetrating the septum. The method further includes delivering a first guidewire from within the lumen of the elongate shaft and across the septum so that a distal end of the first guidewire is positioned in the first chamber and is extractable therefrom. The method additionally includes repositioning the distal end of the elongate shaft within the second chamber so that the distal end of the elongate shaft is adjacent the external wall and penetrating the external wall. The method additionally includes delivering a second guidewire from within the lumen of the elongate shaft and across the external wall so that a distal end of the second guidewire is positioned outside the external wall and is extractable therefrom. The first guidewire is coupleable to the second guidewire to join a path within the second chamber that extends between the penetration of the septum and the penetration of the external wall.

In some embodiments, the elongate shaft includes a needle that is disposed within the lumen of the elongate shaft. The needle is deliverable from the within the lumen of the elongate shaft to penetrate the septum and to penetrate the external wall. In other embodiments, the first guidewire may be advanced from within the lumen of the elongate shaft in order to penetrate the septum and the second guidewire may be advanced from within the lumen of the elongate shaft in order to penetrate the external wall. In some embodiments, an additional elongate shaft is advanced from outside the heart and through the vasculature into the first chamber so that a distal end of the additional elongate shaft is disposed in the first chamber. The distal end of the additional elongate shaft may be coupled, within the first chamber of the heart, with the distal end of the first guidewire so as to join a path of the first guidewire with a path of the additional elongate shaft. The additional elongate shaft may have a flexible body that is slidably coupled to the additional elongate shaft and that is configured for in situ coupling with the distal end of the first guidewire. The flexible body may be a snare device that is slidably disposed within a lumen of the additional elongate shaft and that is axially advanceable therefrom. The snare device may have an opening that is configured for capturing the first guidewire within the first chamber and the snare device may be biased to expand from a low profile configuration when released in the first chamber in order to expand the opening.

An external elongate shaft may be advanced from outside the patient to the external wall of the second chamber so that a distal end of the external elongate shaft is disposed adjacent the external wall. The external elongate shaft may be coupled with the distal end of the second guidewire for extracting the second guidewire from the external wall to outside the patient body. The external elongate shaft may include a second snare device that is slidably disposed within a lumen of the external elongate shaft and that is axially extendable therefrom. The second snare device may be positionable on the external wall of the second chamber for coupling with the second guidewire.

A first anchor may be advanced from outside the heart along the joined path of the first guidewire and the second guidewire so that the first anchor is positioned against the septum within the first chamber. The first anchor is typically coupled with a tension member that extends from the first anchor, through the septum, through the second chamber, and through the external wall when the first anchor is positioned against the septum. A second anchor may be advanced from outside the heart along the tension member so that the second anchor is positioned against the external wall. The second anchor may be slidably coupled with the tension member. Tension may be applied between the first anchor and the second anchor via the tension member in order to urge the septum and the external wall to engage. The first anchor may be advanced from outside the heart via an alignment device that includes: an elongate body, an opening in a distal end of the elongate body within which the first anchor is positioned; and a reposition mechanism. The distal end of the alignment device may be advanced within the first chamber and the first anchor may be deployed, via the reposition mechanism, from the opening of the elongate body to align the first anchor with the septum within the first chamber. The first anchor may be retracted within the opening of the elongate body, via the reposition mechanism, in order to reposition the first anchor about the septum. The reposition mechanism may include a guidewire or cable that is slidably disposed within a lumen of the elongate body and within an axial lumen of the first anchor. The elongate body may be configured so that distal sliding of the guidewire or cable within the lumen of the elongate body causes a portion of the guidewire or cable to protrude outwardly from the opening of the elongate body, thereby causing the first anchor to be retractably deployed from the opening.

A coupling member may be secured to a proximal end of the first guidewire and to a proximal end of the second guidewire to couple the first guidewire to the second guidewire. In other embodiments, the first guidewire may be a first end of a single elongate guidewire and the second guidewire may be a second end of the single elongate guidewire so that the first and second guidewires are opposing ends of the same guidewire.

External walls of an apex of the heart may be penetrated via a needle of an apical anchor device. The apical anchor device may include an elongate tension member having an anchor attached to a proximal end and the needle attached to a distal end thereof. The needle may be pulled through the external walls of the apex of the heart in order to advance the anchor, via the elongate tension member, into engagement with one of the external walls of the apex. The needle may have a curved or arcuate configuration and may be made of a more rigid material than the elongate tension member. The anchor of the apical anchor device may be pivotably coupled to the proximal end of the elongate tension member so that the anchor is pivotable from a low-profile configuration to a deployed configuration.

According to another aspect, a method for treating a heart within a patient is provided. The heart has first and second chambers with a septum there between and the second chamber has an exterior wall. The method includes advancing a first elongate shaft from outside the patient and through the vasculature so that a distal end of the first shaft is disposed in the first chamber. A second elongate shaft is advanced from outside the heart and through the vasculature into the second chamber so that a distal end of the second elongate shaft is disposed in the second chamber. The second elongate shaft has a proximal end and a lumen that extends between the proximal end and the distal end. The distal end of the second elongate shaft is positioned adjacent the septum and the septum is penetrated. A first guidewire is delivered from within the lumen of the second elongate shaft and across the septum so that a distal end of the first guidewire is positioned in the first chamber and is extractable therefrom. The distal end of the first elongate shaft is coupled, within the first chamber of the heart, with the distal end of the first guidewire so that the first guidewire is extractable from the first chamber via the first elongate shaft. The distal end of the second elongate shaft is repositioned within the second chamber so that the distal end of the second elongate shaft is positioned adjacent the external wall and the external wall is penetrated. A second guidewire is delivered from within the lumen of the second elongate shaft and across the external wall so that a distal end of the second guidewire is positioned outside the external wall and is extractable therefrom to a position outside the patient body. The first guidewire is coupleable to the second guidewire to form a path that extends from outside the patient body at a first location, into the first chamber, through the septum, through the second chamber, through the external wall, and outside the patient body at a second location.

A first anchor may be advanced from outside the patient body at the first location along the formed path so that the first anchor is positioned against the septum within the first chamber. The first anchor is coupled with a tension member that extends from the first anchor, through the septum, through the second chamber, and through the external wall when the first anchor is positioned against the septum. A second anchor is slidably coupled with the tension member. The second anchor is advanced along the tension member from outside the patient body at the second location so that the second anchor is positioned against the external wall. Tension is applied between the first anchor and the second anchor via the tension member in order to urge the septum and the external wall into engagement.

A coupling member may be secured to a proximal end of the first guidewire and a proximal end of the second guidewire to couple the first guidewire to the second guidewire. In other embodiments, the first guidewire may be a first end of a single elongate guidewire and the second guidewire may be a second end of the single elongate guidewire so that the first and second guidewires are opposing ends of the same guidewire. In some embodiments, penetrating the septum may be achieved via advancing a needle from within the lumen of the second elongate shaft and through the septum and penetrating the external wall may be achieved via advancing the needle from within the lumen of the second elongate shaft and through the external wall. In other embodiments, penetrating the septum may be achieved via advancing the first guidewire through the septum and penetrating the external wall may be achieved via advancing the second guidewire through the external wall.

According to another aspect, an anchor device for treating a heart within a patient includes a tension member, an anchor that is attached to a proximal end of the tension member, and a needle that is attached to a distal end of the tension member. The needle has a tissue penetrating tip that is configured for penetrating through external walls of an apex of the heart. The tension member couples the needle and the anchor is configured to be tensioned after the needle penetrates through the external walls of the apex to advance the anchor into engagement with one of the external walls of the apex.

The needle has a curved or arcuate configuration and is made of a more rigid material than the tension member. In some embodiments, the needle is made of metal. The anchor of the anchor device is axially affixed and pivotably coupled to the tension member such that the anchor is able to pivot from a low-profile configuration to a deployed configuration. An additional anchor is removably coupleable with the distal end of the tension member. The additional anchor is slidable proximally along the tension so as to engage an opposing external wall of the apex of the heart to close off a lower portion of the heart.

According to another aspect, a method for applying an anchor to an apex of the heart includes penetrating external walls of the apex of the heart with a needle of an apical anchor device. The apical anchor device includes: a tension member, an anchor attached to a proximal end of the tension member, and the needle attached to a distal end of the tension member. The method also includes pulling the needle through the external walls of the apex of the heart so as to advance the anchor, via the tension member, toward the apex of the heart and engaging one of the external walls of the apex of the heart with the anchor.

The needle has a curved or arcuate configuration and is made of a more rigid material than the tension member. In some embodiments, the needle is made of a metal. The anchor of the apical anchor device is pivotably coupled to the proximal end of the tension member so that the anchor is pivotable from a low-profile configuration to a deployed configuration. In some embodiments, the anchor is a first anchor and the method further includes coupling a second anchor with the distal end of the tension member, sliding the second anchor proximally along the tension into engagement with an opposing external wall of the apex of the heart, and applying tension to the first and second anchors, via the tension member, to bring the opposing external walls into apposition.

BRIEF DESCRIPTION OF THE DRAWINGS

The present invention is described in conjunction with the appended figures:

FIG. 4 illustrates a ventricle apex anchor member or apical anchor device of the anchor delivery system.

FIG. 5 illustrates an introducer assembly including an introducer catheter and a dilator catheter of the anchor delivery system.

FIGS. 41-65 illustrate fluoroscopic images taken during the study of the specimen of FIGS. 22-41.

Figure 1A:
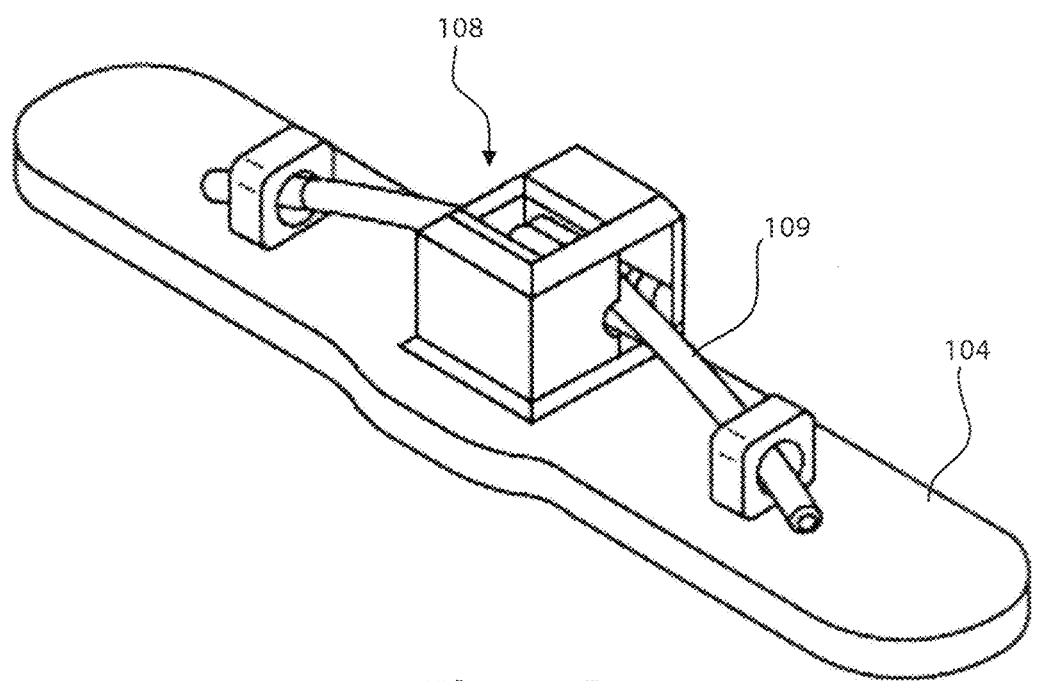
FIGS. 1A-B illustrate a pair of anchor members of an anchor delivery system that may be employed in performing the procedures described herein.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments herein generally provide improved medical devices, systems, and methods. Exemplary embodiments of the devices are described for use in reducing the distance between a region along the septum and a region of an external wall of the left and/or right ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. The procedures typically result in reduction of left ventricle volume, primarily as a result of a decrease in LV circumference, which conveys lower wall tension. Lower wall tension is a recognized cause of heart failure progression. The procedures further eliminate substantial risks present in standard Surgical Ventricular Reconstruction (SVR). The procedures are also a less complex treatment than SVR and may be administered via "minimal-access surgery."

In reconfiguring abnormal heart geometry, it may be desirable to place permanent cardiac implants or anchors about the heart for the purpose of reconfiguring the geometry of the heart. The implants, when properly deployed, may act through the exclusion of a discrete portion of the circumference of the ventricular wall, and therefore, a decrease in the size of the chamber. Disclosed herein is a procedure that allows a physician to implant heart anchors and/or other components into the heart utilizing a closed chest, beating heart, minimally invasive technique. More specifically, the procedures described herein are achieved primarily via catheters that are positioned within the heart via percutaneous arterial and/or venous access. The procedures minimize or eliminate the need for catheters that are positioned external to the heart and that are used to puncture or penetrate the heart. A heart implant system is employed, which includes implantable components and delivery system components that are used to place and secure those implantable components within the heart.

An advantage of the procedures described herein is that the procedures do not require cardiopulmonary bypass. The procedures also do not require cutting into the left ventricle (LV) wall (ventriculotomy) as is often required for standard surgical treatments. This eliminates the risks of ventriculotomy suture-line bleeding and the introduction of air into the heart. Additionally, many of the embodiments herein do not require an external puncture or penetration of the heart. Rather, all of the heart tissue penetration, or a substantial majority thereof, may be achieved via catheters or other devices that are inserted through the vasculature and positioned within the heart. As a result, the procedures are significantly less invasive than traditional procedures and result in less patient scarring and/or decreased trauma or damage.

The procedure may be used for exclusion of acontractile ventricular scar and/or to geometrically reconfigure the left ventricle. Since the procedures are performed from outside of the beating, functioning heart, the entire process is typically image guided. It may be desired to have C-arm fluoroscopy and/or one of the following imaging devices: Trans-Esophageal Echocardiography (TEE); Surface Echocardiography; Intra-cardiac Echocardiography (ICE), and the like. Voltage mapping may also or alternatively serve as an adjunct. Cardiac surfaces and chamber boundaries may be visualized via echocardiography while devices are pinpointed via fluoroscopy. Visualization of the epicardial surface of the heart may be performed through a mini-thoracotomy and multiple ports. If ports are utilized, an endoscopic tower, thoracoscope, and light source may be used.

Exemplary Components

Figure 1B:
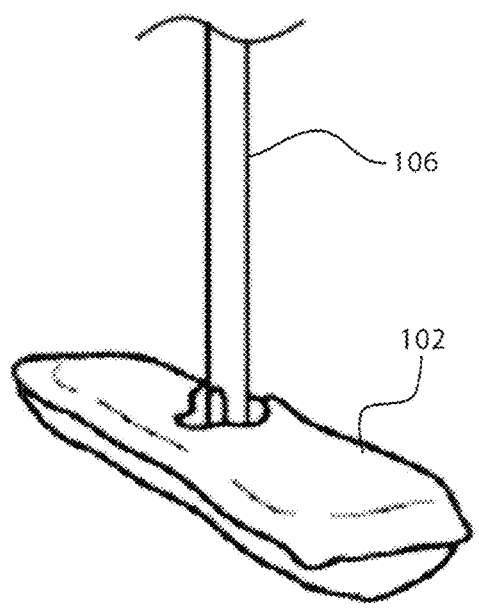

Various components of the anchor delivery system, which may be used in administering the procedure, are described below. As shown in FIGS. 1A-B, the implantable components include a series of anchor pairs that may be made of titanium and covered in polyester cloth. The anchors include a first or septal anchor 102 and a second or epicardial anchor 104. The septal anchor 102 is hinged or pivotably coupled to a tension member or tether 106 (hereinafter tension member 106). The epicardial anchor 104 is positionable about the tension member 106 by inserting the tension member 106 within a release mechanism 108 that is configured to enable the epicardial anchor 104 to slide about the tension member 106 and to lock or secure the epicardial anchor 104 about the tension member 106. In reconfiguring the heart geometry, the anchor pairs are connected to each other by the tension member 106, which may be made of poly-ether-ether-ketone (PEEK). The separation distance between the anchor pairs, 102 and 104, may be infinitely adjustable and may be determined by the location of the epicardial anchor 104 relative to the septal anchor 102 as described herein below. The septal anchor 102 pivots about the end of the tension member 106 to facilitate placement of the septal anchor 102 via a septal anchor delivery device 200. After insertion of the septal anchor 102 within the heart, the septal anchor 102 may pivot or rotate to a perpendicular orientation as shown in FIG. 1B. The release mechanism 108 of the epicardial anchor 104 houses or includes a cam with a reversible locking mechanism that allows apposition of the two anchors, 102 and 104, at a continuum of positions. The septal anchor 102 is positionable over a guidewire, which enables transvascular placement of the septal anchor 102. Exemplary embodiments of septal and epicardial anchors are further described in U.S. Pat. No. 8,491,455, entitled "Treating Dysfunctional Cardiac Tissue", and in U.S. Pat. No. 8,979,750, entitled "Trans-Catheter Ventricular Reconstruction Structures, Methods, and Systems for Treatment of Congestive Heart Failure and Other Conditions", the entire disclosures of which are incorporated by reference herein.

Figure 2:
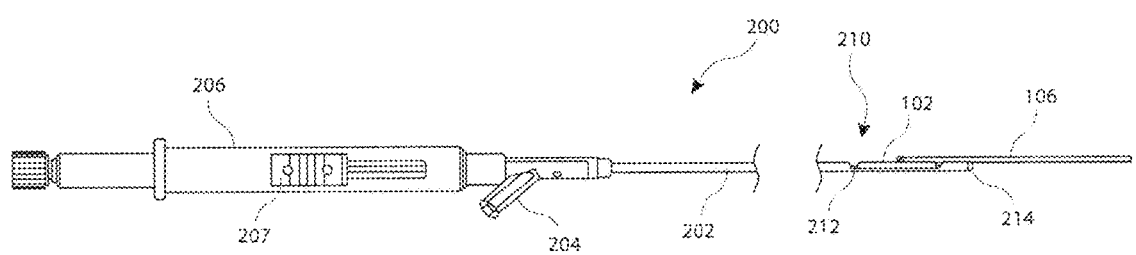
FIG. 2 illustrates a septal anchor delivery assembly or device of the anchor delivery system.

FIG. 2 illustrates a septal anchor delivery assembly or device 200 (also referred to herein as an alignment device). The septal anchor delivery device 200 is used with the septal anchor 102 and tension member 106 to place these components within a chamber of the heart (e.g., within the right ventricle) and adjacent the septal wall of the heart. The septal anchor delivery device 200 is employed within the heart chamber to align the septal anchor 102 about the septal wall as desired. The septal anchor delivery device 200 is designed so that the septal anchor 102 may be deployed and retracted from the septal anchor delivery device 200 multiple times if necessary to ensure a proper placement of the septal anchor 102 about the septal wall.

The septal anchor delivery device 200 includes a push tube assembly or elongate body 202, a flush port 204, and a handle assembly or reposition mechanism 206. The elongate body 202 includes a window or opening 210 within which the septal anchor 102 is positioned. A cable 212 is slidably disposed through a lumen of the elongate body 202 and through an axial lumen of the septal anchor 102. A distal tip 214 of the elongate body 202 is capped or plugged to prevent the cable 212 from extending distally beyond the distal tip 214. The handle assembly or reposition mechanism 206 (hereinafter handle assembly 206) is operationally coupled with the elongate body 202 so that a first operation of the handle assembly 206 causes the septal anchor 102 to be retractably deployed from the opening 210 of the elongate body 202. Specifically, the first operation of the handle assembly 206, which may consist of sliding a button 207, causes the cable 212 to slide within the lumen of the elongate body 202. Sliding of the cable 212 within the lumen causes the cable 212 to engage with the distal tip 214, which causes the cable 212 and septal anchor 102 to bow, protrude, or flex outward from the opening 210. The septal anchor may be repositioned or retracted within the opening 210 by a second operation of the handle assembly 206 (e.g., sliding the button 207 in an opposite direction), which causes the cable 212 to slide proximally within the lumen of the elongate body 202 and further causes the cable 212 and septal anchor 102 to axial align with the elongate body 202. Thus, the handle assembly 206 may be employed to deploy and retrieve the septal anchor 102 from the opening 210 as necessary. A third operation of the handle assembly 206 may also be performed to permanently release or uncouple the septal anchor 102 from the opening 210. The third operation of the handle assembly 206 may cause the cable 210 to retract fully through the lumen of the septal anchor 102, thereby uncoupling or detaching the septal anchor 102 from the septal anchor delivery device 200.

As illustrated in FIG. 2, the septal anchor 102 and septal anchor delivery device 200 are typically inserted through the vasculature with the tension member 106 advanced distally of the septal anchor 102. After the septal anchor 102 is deployed in the right ventricle, the tension member 106 extends across the septum and out of the left ventricle. The epicardial anchor 104 may then be inserted onto the tension member 106 and advanced towards the septal anchor to appose the septal and left ventricle walls. The flush port 204 may be a connector (e.g., Y-connector) that allows flushing of the system. An exemplary embodiment of the septal anchor delivery device 200 is further described in U.S. patent application Ser. No. 15/259,375, filed Sep. 8, 2016, entitled "Systems and Methods for Deploying a Cardiac Anchor," the entire disclosure of which is incorporated by reference herein.

Figure 3:
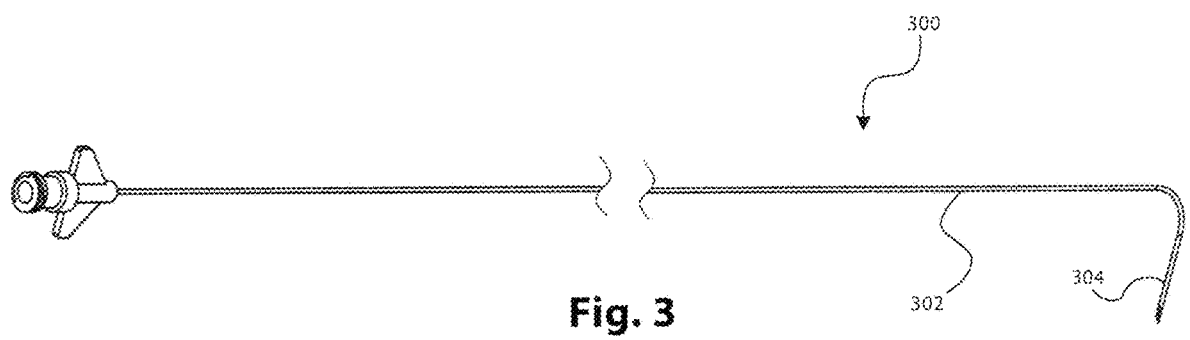
FIG. 3 illustrates a trans-septal needle of the anchor delivery system.

FIG. 3 illustrates a trans-septal needle 300 that may be employed in the anchor delivery system. The trans-septal needle 300 has an elongate body 302 with a needle 304 positioned on a distal end thereof. The needle 304 and/or a portion of the elongate body 302 may have a curved or arcuate configuration as illustrated. The trans-septal needle 300 may have an approximate length of about 33.5 inches and may include 21 Ga. Nitinol tubing and/or 18 Ga. stainless steel tubing. The trans-septal needle 300 may be advanced into the left ventricle via a left ventricular access catheter (e.g., the second catheter 1002, the introducer catheter 510, dilator catheter 520, and the like). Specifically, the trans-septal needle 300 may be slidably disposed within a lumen of the left ventricular access catheter. The trans-septal needle 300 may be deployed from the lumen of the left ventricular access catheter to penetrate a wall of the heart, such as the septal and external walls as described herein. The penetration of the septal wall allows for accurate placement of a guidewire in a desired location on the septum and inside the right ventricle.

FIG. 4 illustrates a ventricle apex anchor member or apical anchor device 400 (hereinafter apex anchor member 400) of the anchor delivery system. The apex anchor member 400 includes an implantable pivoting anchor 402 that is pivotably attached to one end of an elongate tether or tension member 404. The apex anchor member 400 also includes a needle 406 or perforation member that is disposed on an opposite end of the tension member 404. The needle 406 is typically arcuate or curved shape, which aids in penetrating the needle through the wall of the apex.

The needle 406 has a tissue penetrating distal tip that is configured for penetrating through external walls of the heart apex. The tension member 404 couples the needle 406 and the anchor 402 and is configured to be tensioned after the needle 406 penetrates through the external walls of the apex. Tensioning of the tension member 404 causes the anchor 402 to advance into engagement with one of the external walls of the apex, such as for implanting on the right side of the apex of the heart. In some embodiment, the tension member 404 may be approximately 43 cm in length. Once the anchor 402 is deployed, the tension member 404 may extend across the apex. The needle 406 may then be removed from the tension member 404 and discarded, such as by cutting the tension member 404 at the joint of the needle 406 and tension member 404. An epicardial anchor (e.g., 104) may be inserted onto the tension member 404 and advanced towards the pivoting anchor 402 to appose the apical walls.

FIG. 5 illustrates an introducer assembly 500 that may be employed in the anchor delivery system. The introducer assembly 500 includes an introducer catheter 510 (e.g., 14 Fr introducer catheter) and a dilator catheter 520. The introducer assembly 500 may be used to provide right-side superior vena cava (SVC) access and/or may provide access to the left ventricle access via standard percutaneous methods. For example, the introducer catheter 510 may function as a conduit for the insertion of "right-side devices" or left ventricle devices used for the trans-myocardial guidewire placement described herein. The dilator catheter 520 may be employed to widen an access aperture within tissue for delivery of the introducer catheter 510. The introducer assembly 500 may be used in conjunction with a guidewire (e.g., 0.038" guidewire). Once access is attained into the SVC or aorta, the dilator catheter 520 may be removed leaving the introducer catheter 510 in place. The introducer catheter 510 and/or dilator catheter 520 may be inserted within, or otherwise access, the jugular vein and/or subclavian artery. Exemplary embodiments of an introducer catheter and dilator catheter are described in the '750 patent, which is incorporated by reference herein.

Figure 6:
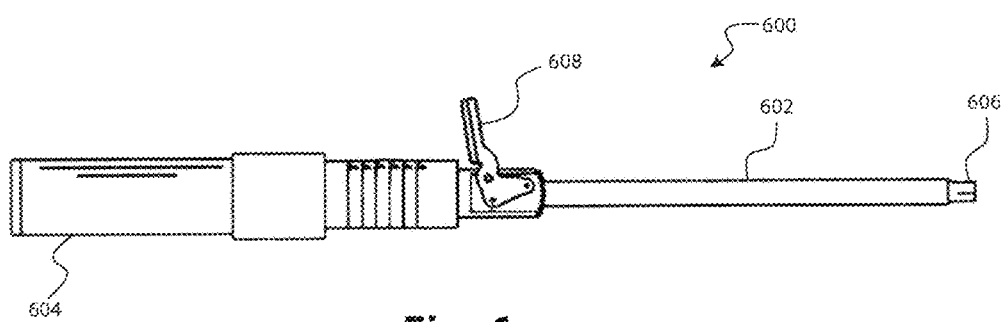
FIG. 6 illustrates a transthoracic force gauge or axial force-application tool of the anchor delivery system.

FIG. 6 illustrates a transthoracic force gauge or axial force-application tool 600 (hereinafter force gauge 600) that may be employed in the anchor delivery system to deliver and apply a desired force to the epicardial anchor 104. The force gauge 600 includes a handle 604 and an elongate body 602 that is configured to slide over the tension member 106 and releasably couple with the epicardial anchor 104. The elongate body 602 includes a lumen within which the tension member 106 is positioned to allow the elongate body 602 to slide over the tension member. The force gauge 600 releasably engages with the epicardial anchor 104 via a coupling mechanism 606 that is disposed on the distal end of the elongate body 602. The force gauge 600 is configured to adjust the epicardial anchor 104 between a variable force mode and a set-force mode by actuating the cam of the epicardial anchor's release mechanism 108 to lock or secure the epicardial anchor 104 to the tension member 106 or to allow the epicardial anchor to move freely over the tension member 106 in both a distal direction toward the heart and a proximal direction away from the heart. The coupling mechanism 606 is configured to grip or engage rod members 109 of the epicardial anchor 104 in order to actuate the release mechanism's cam. The coupling mechanism 606 is operationally coupled with a lever 608 that may be actuated to adjust the epicardial anchor 104 between the variable force mode and the set-force mode.

Advancing the epicardial anchor 104 toward the heart and into engagement with the left ventricle wall is performed to draw the septal and left ventricle walls together in apposition. The force gauge 600 is further configured to deliver or apply a desired anchor migration inhibiting force (typically between 0-6 Newtons) between the septal anchor 102 and epicardial anchor 104 while drawing the septal wall together with the left ventricular wall. An exemplary embodiment of a force gauge is further described in U.S. Pat. No. 9,173,711, entitled "Cardiac Implant Migration Inhibiting Systems," and in U.S. patent application Ser. No. 14/473,556, filed Aug. 29, 2014, entitled "Heart Anchor Positioning Devices, Methods, and Systems for Treatment of Congestive Heart Failure and Other Conditions," the entire disclosures of which are incorporated by reference herein.

Figure 7:
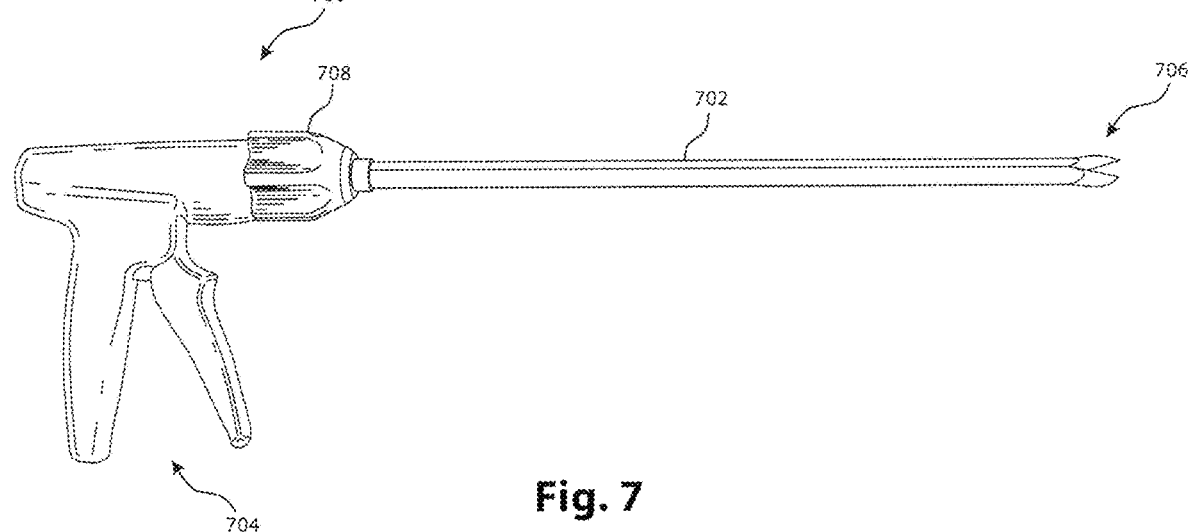
FIG. 7 illustrates a tether or tension member cutter device of the anchor delivery system.

FIG. 7 illustrates a tether or tension member cutter device 700 (hereinafter tether cutter 700) that may be employed in the anchor delivery system to cut or sever the tension members, 106 and 404. The tether cutter 700 includes a handle 704 that is attached to a proximal end of an elongate tube 702. A cutting blade 706, or a pair of cutting blades, is disposed at or on the distal end of the distal tube 702. The tether cutter 700 is a cutting tool that is operable to sever the tension members, 106 and 404, that attach the respective anchors together as described herein. The tether cutter 700 may be used with one hand while the user is holding the tension member, 106 or 404, under light tension. The tether cutter 700 has a rotating head or knob 708, which repositions the cutting blade 706 and thereby allows cutting of the tension member, 106 or 404, from various locations and angles. The tether cutter 700 may be operated from outside the patient's body while the cutting blade 706 is positioned near the patient's heart. In some embodiments, the rotatable knob 708 may have a diameter of about 33 mm and the tether cutter 700 may have an overall length of approximately 431 mm. The elongate tube 702 may have a length of approximately 292 mm and a diameter of approximately 10 mm. The handle 704 may have a width of about 28 mm, a height of about 126 mm, and a length of about 70 mm.

Figure 8:
FIG. 8 illustrates a snare device or flexible body of the anchor delivery system.

FIG. 8 illustrates a snare device or flexible body 800 that may be employed in the anchor delivery system to snare or capture a guidewire within a chamber of the heart. In some embodiments, the snare device 800 includes a pair of loops that are arranged so that each loop is roughly orthogonal to the other loop. The pair of loops form a three dimensional basket shaped object, which enables easier snaring or capturing of the guidewire since the basket is less directionally dependent than an individual loop. Specifically, it is significantly easier to insert the guidewire through the three dimensional snare than to insert the guidewire through a two dimensional loop. Each loop of the snare device 800 is retractable within a lumen of an elongate catheter body 802. Retraction of loops with the elongate catheter body 802 causes the three dimensional basket to contract as it is retracted within the elongate catheter body 802, which snares or captures the guidewire positioned through the three dimensional basket.

The snare device 800 enables in situ coupling of the guidewire and a catheter (e.g., first catheter 1002) that is positioned within the chamber as described herein. The coupling of the guidewire and catheter may be done to join separate paths through the heart for delivery of the septal and epicardial anchors, 102 and 104. The three dimensional basket is axially advanceable from the elongate catheter body 802. The three dimensional basket includes an opening that is configured for capturing the guidewire within the chamber of the heart. The three dimensional basket is biased to expand from a low profile configuration to an open configuration when it is released or axially advanced from the lumen of the elongate catheter body 802.

Some or all of the above components may be used in performing the procedures described herein. Additional components may also be used in performing the procedures herein, some of which will be described below.

Exemplary Procedure

For ease in describing the procedures, the left ventricle will be referred to hereinafter as LV and the right ventricle will be referred to as RV. The procedures are illustrated in FIGS. 9-21. The procedures described herein provide a novel approach to delivering septal and epicardial anchors, 102 and 104, to desired positions about the heart. Specifically, the anchors are delivered by inserting an access wire through the septum and LV wall. Unlike prior methods, the access wire is inserted through the septum and LV wall via a first catheter 1002 that is positioned within the RV and a second catheter 1004 that is positioned in the LV. A distal end of the first catheter 1002 is positioned in the RV via venous access (e.g., the jugular vein, femoral vein, and the like). For example, the first catheter 1002 may percutaneously accesses the right internal jugular vein (or another venous access) and then be guided into, or otherwise access, the right ventricle via the superior vena cava, right atrium, and tricuspid valve. Alternatively, the venous access may include the subclavian vein and superior vena cava, the femoral vein and inferior vena cava, and the like. In some embodiments, the first catheter 1002 may be an introducer catheter 510 and/or dilator catheter 520. In other embodiments, the first catheter 1002 may be a steerable catheter or an assembly that includes some combination of an introducer catheter 510, a dilator catheter 520, and a steerable catheter.

Guidewires may be employed in advancing the first catheter 1002 through the vasculature and within the RV and/or for other procedures described herein. For example, a pulmonary artery catheter (e.g., Swan-Ganz catheter) may be inserted through the tricuspid valve and into the pulmonary artery. Two guidewires (e.g., 0.025 wires) may then be passed into the pulmonary artery via the pulmonary artery catheter. The pulmonary artery catheter (not shown) may then be removed while the two guidewires (not shown) remain positioned in the pulmonary artery. The first catheter 1002 may then be passed, along with other components such as a guiding catheter or snare sheath, over one of the guidewires to the pulmonary artery. The first catheter 1002 may be used to maintain intra-RV stabilization at the RV apex. The guidewire over which the first catheter was passed may then be removed.

A distal end of the second catheter 1004 is positioned in the LV via arterial access (e.g., subclavian artery). For example, the second catheter 1004 may percutaneously access the carotid artery (or other arterial access) and then be guided into, or otherwise access, the left ventricle via the subclavian artery, aorta, and aortic valve. Alternatively, the arterial access may include the subclavian artery, the femoral artery, or axillary artery, or the catheter may access the femoral vein and cross the arterial septum to gain access to the left ventricle. In some embodiments, a Pigtail catheter may be employed to aid in accessing the LV. Regardless of the access chosen, the first catheter 1002 is positioned in the RV and the second catheter 1004 is positioned in the LV. In some embodiments, the second catheter 1004 may be an introducer catheter 510 and/or dilator catheter 520. In other embodiments, the second catheter 1004 may be a steerable catheter or an assembly that includes some combination of an introducer catheter 510, a dilator catheter 520, and a steerable catheter. Regardless of the embodiment, the first and second catheters, 1002 and 1004, include elongate shafts that are configured for advancement through the vasculature from outside the patient's body. The first and second catheters, 1002 and 1004, also typically include a proximal end and a lumen that extends between the proximal end and the distal end.

Figure 9:
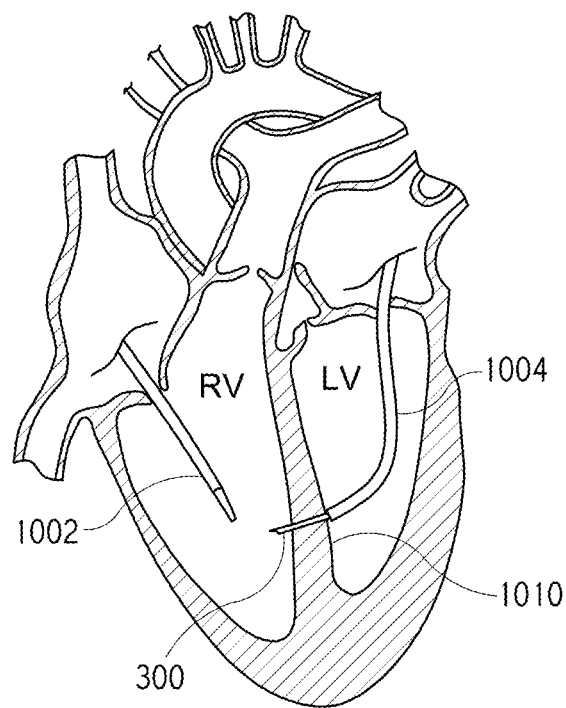
FIGS. 9-21 illustrate a procedure for advancing one or more catheters percutaneously within a body in order to deliver anchors to one or more walls of the heart in order to therapeutically treat the heart.

As shown in FIG. 9, the second catheter 1004 is positioned in the LV so that the distal end of the second catheter 1004 is steered toward or positioned adjacent the septum 1010. The septum is then penetrated via the trans-septal needle 300, an RF device, and the like. The second guidewire (not shown) may function to provide a guide to the anterior wall of the RV. For example, when the second guidewire is placed out of the right ventricular outflow tract (RVOT) through the Pulmonary valve, it causes a portion of the second guidewire to sit along the anterior wall of the RV. This may be important in locating or identify an ideal location for the septal anchors 102 along the septum 1010. In a specific embodiment, the trans-septal needle 300 is advanced distally from the lumen of the second catheter 1004 in order to penetrate the septum. A first access wire or guidewire 1012 (e.g., 0.014" wire) is then inserted through the penetration of the septum 1010 so that a distal end of the first access wire or guidewire 1012 (hereinafter first access wire 1012) is positioned in the RV. The first access wire 1012 is typically disposed within a lumen of the trans-septal needle 300. The second catheter 1004 provides sufficient column strength for the trans-septal needle 300 to penetrate the septum. The trans-septal needle 300 likewise provides sufficient column strength for the first access wire 1012 to be passed across the septum 1010.

Alternatively, the first access wire 1012 may be advanced through the septum 1010 without the use of the trans-septal needle 300. In such embodiments, the distal end of the second catheter 1004 is positioned against the septum 1010 and the first access wire 1012 is advanced distally from within the lumen of the second catheter 1004. The first access wire 1012 is sufficiently small (e.g., 0.014" wire) so that its distal end is sharp enough to penetrate through the tissue of the septum 1010. The second catheter 1004 provides enough column strength to reinforce the first access wire 1012 and prevent or minimize buckling as the first access wire 1012 penetrates and is advanced through the septum 1010. Eliminating the use of the trans-septal needle 300 reduces the hole or incision that is produced in the septal wall, which minimizes trauma to the tissue and increases patient recovery. It further minimizes hemorrhaging of blood through the incision. The procedure may or may not utilize the trans-septal needle 300 as deemed appropriate by those that are performing the procedure.

In determining an ideal position for the septal and epicardial anchors, 102 and 104, scar margins and other epicardial landmarks may be identified via direct visualization and a target, such as a temporary pacemaker lead, can be placed to mark the scar edge. Alternatively mapping technology such as NavX or Carto can identify the scar by measuring the impedance of the heart wall tissue. The identification of these features may aid in determining where to place the septal and/or epicardial anchors, 102 and 104. Heparin or other drugs may be administered to the patient. Markers may be placed on the LV epicardium to provide a target for the epicardial anchor 104.

Figure 10:
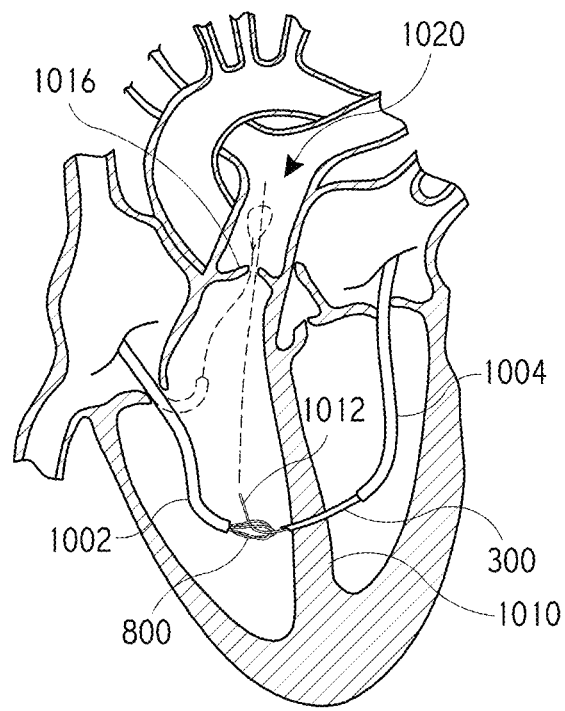

As illustrated in FIG. 10, a capture device, such as the snare device 800, is employed to capture the first access wire 1012 in the RV. For ease in describing the embodiments herein, the capture device will be referred to as the snare device 800, although it should be realized that any other device that is capable of capturing the first access wire 1012 may be employed. In a specific embodiment, the snare device 800 is axially advanced from the lumen of the first catheter 1002, which causes the snare device 800 to expand within the RV. The snare device 800 is typically positioned adjacent the septum at a pre-determined site for penetration of the septum via the trans-septal needle 300. To properly position the snare device 800, the snare device 800 may be positioned in the pulmonary artery by passing the snare device 800 through the lumen of the first catheter 1002 or a guide catheter. The first catheter 1002 and/or snare device 800 may be retracted back from the RVOT through the anterior portion of the septum 1010 until the snare device 800 is positioned in a predetermined or identified position against the septum 1010 for the septal anchor 102. The first access wire 1012 wire is inserted through the penetration and within the RV so that the distal end of the first access wire 1012 is positioned within the opening of the snare device 800. The snare device 800 is then retracted within the lumen of the first catheter 1002 so that the first access wire 1012 is captured, snared, or otherwise engaged with the first catheter 1002.

In some embodiments, the first access wire 1012 may be snared or captured at an alternative location within the heart. For example, reference numeral 1020 illustrates an alternative location for capturing the first access wire 1012. As illustrated in dashed lines, the snare device 800 may be deployed from the first catheter 1002 in a manner that allows the snare device 800 to flow or migrate toward the pulmonary valve 1016. In other embodiments, the distal end of the first catheter 1002 may flow or migrate toward the pulmonary valve 1016. The flow of blood within the RV may cause the snare device 800 and/or distal end of the first catheter 1002 to flow or migrate to this position. The first access wire 1012 may likewise be deployed from the lumen of the second catheter 1004 and trans-septal needle 300 in a manner that allows the first access wire 1012 to flow or migrate toward the pulmonary valve 1016, which may be caused by the flow of blood within the RV. The first access wire 1012 may then be snared or captured by the snare device 800 adjacent the pulmonary valve 1016. Snaring of the first access wire 1012 near the pulmonary valve 1016 may be easier than snaring the first access wire 1012 near the septum 1010 due to the blood causing the various components to naturally migrate toward the pulmonary valve 1016.

Figure 11:
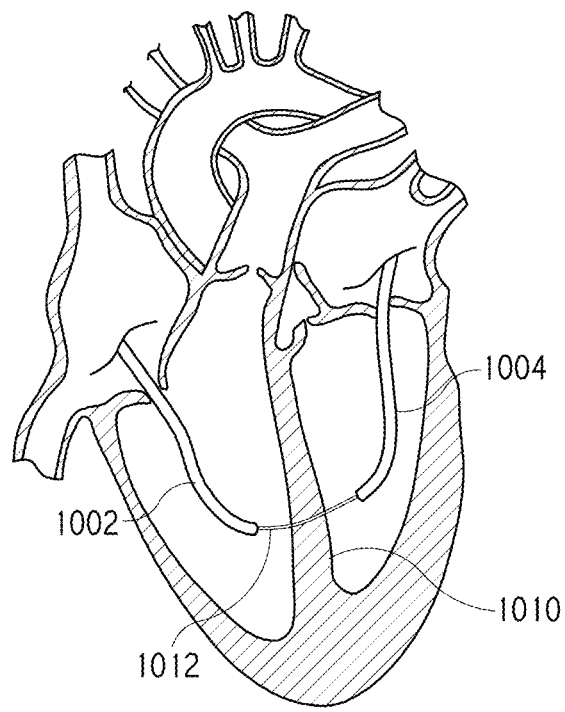

With the first access wire 1012 snared or captured via the snare device 800, the first access wire 1012 is then pulled through the access vein (e.g., jugular vein, femoral vein, and the like) so that proximal and distal ends of the first access wire 1012 are positioned outside the patient's body with a middle portion of the first access wire 1012 extending along a path across the septum, through the RV, and through the access vein. The first access wire 1012 may be pulled through the access vein via retraction of the snare device 800 through the lumen of the first catheter 1002. FIG. 11 illustrates the first access wire 1012 pulled through the access vein in this manner. The first access wire 1012 extends between the first catheter 1002 and the second catheter 1004 and across the septum 1010. A distal end of the first access wire 1012 is positioned externally of the venous access point (e.g., the Jugular vein) while a proximal end of the first access wire 1012 is positioned externally of the arterial access point. A mid-portion of the first access wire 1012 remains disposed through the LV and the venous and arterial access vasculature.

Figure 12:
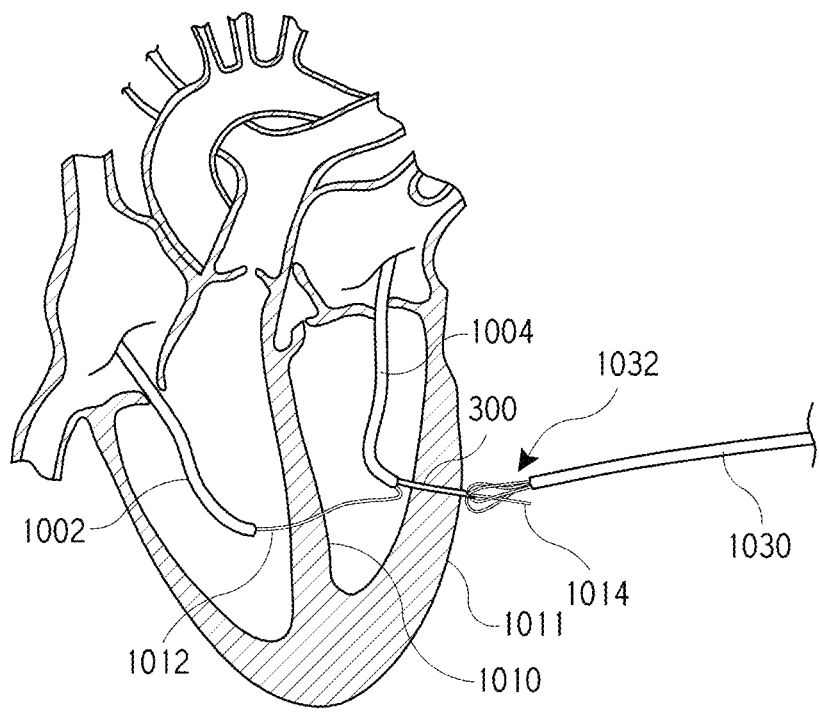

As illustrated in FIG. 12, the distal end of the second catheter 1004 is repositioned or steered toward an external wall 1011 of the LV so that the distal end of the second catheter 1004 is positioned adjacent the external wall 1011. The distal end of the second catheter 1004 may be repositioned adjacent a marker disposed on the LV epicardium. The marker may be provided via a pace lead, radiopaque marker, and the like. The external wall 1011 is then penetrated via the trans-septal needle 300, an RF device, and the like, at the marked location. In a specific embodiment, the trans-septal needle 300 is advanced distally from the lumen of the second catheter 1004 in order to penetrate the external wall 1011. A second access wire or guidewire 1014 (e.g., 0.014" wire) is then advanced through the lumen in the trans-septal needle 300 and through the penetration of the external wall 1011 so that a distal end of the second access wire or guidewire 1014 (hereinafter second access wire 1014) is positioned distally of the external wall 1011.

Alternatively, the second access wire 1014 may be advanced through the external wall 1011 without the use of the trans-septal needle 300. In such embodiments, the distal end of the second catheter 1004 is positioned against the external wall 1011 and the second access wire 1014 is advanced distally from within the lumen of the second catheter 1004. The second access wire 1014 is able to penetrate through the tissue of the external wall 1011 and the second catheter 1004 provides sufficient column strength to reinforce the second access wire 1014 and prevent or minimize buckling as the second access wire 1014 penetrates and is advanced through the external wall 1011. Eliminating the use of the trans-septal needle 300 reduces the hole or incision that is produced in the external wall, which may provide the advantages described herein.

Figure 13:
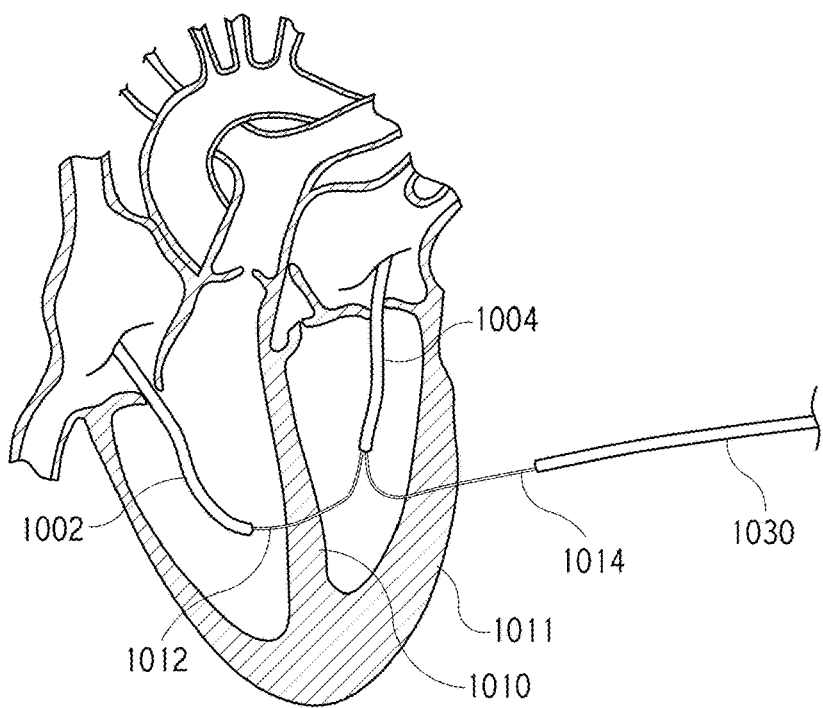

The second access wire 1014 may be extracted from the external wall 1011 via a third catheter 1030 that is positioned outside the patient's body. The third catheter 1030 includes a capture device 1032, such as a snare, to enable the third catheter 1030 to couple with the second access wire 1014 for extraction of the second access wire 1014 from the external wall 1011 to outside the patient body. Specifically, as the second access wire 1014 penetrates and extends beyond the external wall 1011, the second access wire 1014 may be grasped and pulled, via the third catheter 1030, through an access port that is positioned between the patient's ribs so that proximal and distal ends of the second access wire 1014 are positioned outside the patient's body while a middle portion of the second access wire 1014 extends along a path through the arterial access, through the LV, and across the external wall 1011. After extraction of the second access wire 1014, a proximal portion of the second access wire 1014 remains disposed through the external wall 1011 and arterial access vasculature while a distal end of the second access wire 1014 is positioned outside the body. FIG. 13 illustrates the second access wire 1014 being extracted from the external wall 1011 as described herein. FIG. 13 also illustrates the first access wire 1012 positioned across the septum 1010 as described herein.

In some embodiments, the capture device 1032 of the third catheter 1030 is a second snare device that is slidably disposed within a lumen of the third catheter 1030 and that is axially extendable or advanceable therefrom. The second snare may be positioned on the external wall 1011 of the LV for coupling with the second access wire 1014. The second snare may be a three dimensional basket snare that is similar to the snare device 800 of FIG. 8, or may include a single loop component. The single loop component may be substantially easier to position about the heart since the second access wire 1014 is being captured external to the heart.

As described herein, the delivery of the access wire across the RV and LV may be performed entirely within the heart. Specifically, the delivery of the access wire across the RV and LV may be performed via the first catheter 1002 positioned in the RV and the second catheter 1004 positioned in the LV. These catheters, and/or any other necessary components, access the heart percutaneously through venous and/or arterial vasculature. As such, the delivery of the access wire does not require penetration of an external catheter, needle, or other component, through the heart wall. Rather, the only process external to the heart that may be needed is grasping of the second access wire extending from the heart surface and extraction of the second access wire through the access port in the ribs.

Figure 14:
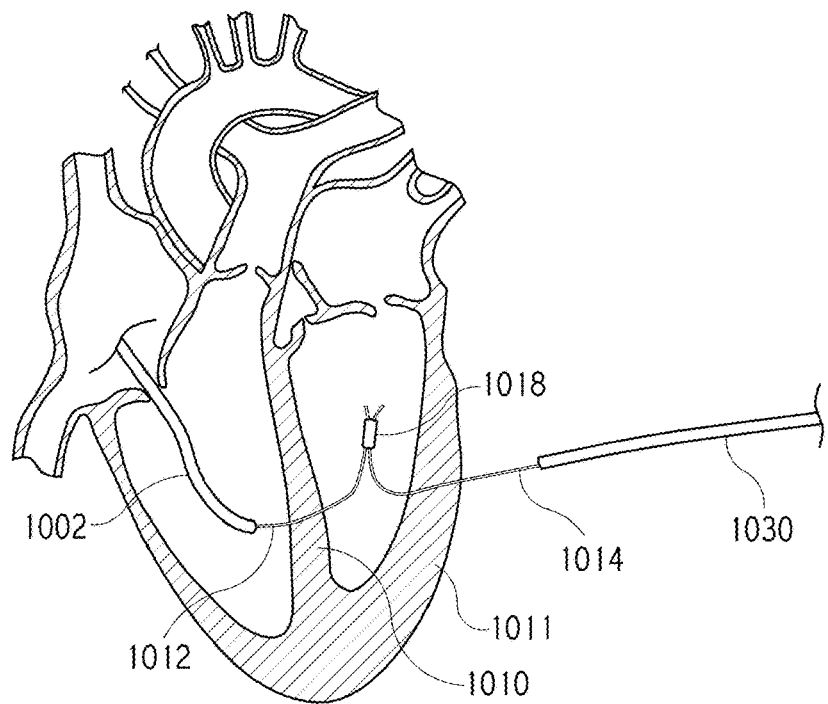

As illustrated in FIG. 14, with the first access wire 1012 and second access wire 1014 positioned through the respective heart wall, the proximal end of the first access wire 1012 may be coupled or attached with the proximal end of the second access wire 1014 via a fastening component 1018, such as a crimp or any other known fastener. The proximal ends of the first access wire 1012 and second access wire 1014 may be secured together from outside the patient's body, or within the arterial access, in order to couple or connect said wires. With the proximal ends coupled together, the crimped section of the wires (i.e., the section corresponding to fastening component 1018) may be pulled through the arterial access (e.g., subclavian artery) and within the LV (or RV if desired) as shown in FIG. 14. The coupled first and second access wires, 1012 and 1014, join the paths of said wires and form or function as a single wire (i.e., 1019 of FIG. 15) that extends from a first side of the patient, through the venous access, through RV, across the septum, across the LV, through the LV wall, through the access port in the ribs, and externally of a second side of the patient.

Figure 15:
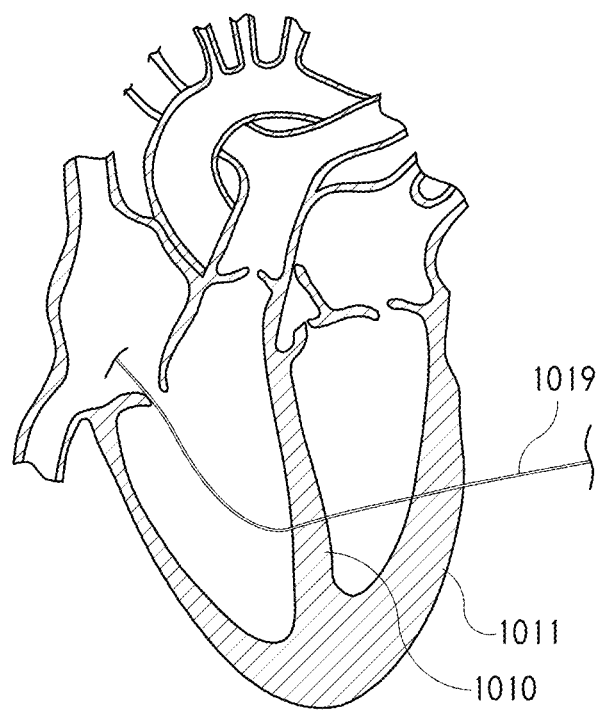

FIG. 15 illustrates the single wire 1019 that is formed via joining the first and second access wires, 1012 and 1014. The single wire 1019 extends across the heart and through the patient's body and vasculature as described herein. Although the single wire 1019 is illustrated without the fastening component 1018, it should be understood that the fastening component 1018 may be present within the LV, RV, or elsewhere within the body. In other embodiments, the first and second access wires, 1012 and 1014, may be pulled through the vasculature so that the fastening component 1018 is removed from within the body. When the fastening component 1018 is removed from the body, the single wire 1019 may be a solitary or unitary wire or cable without any broken or separate sections.

In an alternative embodiment, the proximal ends of the first and second access wires, 1012 and 1014, are not coupled or attached together. Rather, in the alternative embodiment, the first access wire 1012 is one end of a single access wire/guidewire and the second access wire 1014 is an opposite end of the single access wire/guidewire. In such an embodiment, the proximal ends of the first and second access wires, 1012 and 1014, do not need to be coupled since they are opposite ends of the same wire. Extraction of the second access wire 1014 from the patient's body as describe herein may cause a central portion of the single wire to be pulled into the LV. In the alternative embodiment, the single wire would be represented by the single wire 1019 of FIG. 15. The first and second access wires, 1012 and 1014, may be opposing ends of the same wire by back loading the single wire within the second catheter 1004.

In yet another alternative embodiment, the third catheter 1030 may be used to penetrate the external wall 1011 and capture the second access wire 1014. The third catheter 1030 may be a small introducer catheter (e.g., 7 Fr introducer) that is inserted through the external wall 1011 from outside the heart. The third catheter 1030 may be positioned in an area marked for placement of the epicardial anchor 104 on the LV epicardium. In such embodiments, the capture device 1032 (e.g., second snare) may be placed within or adjacent the LV apex. A proximal end of the first access wire 1012 may then be delivered or positioned in the capture device 1032 from the second catheter 1004 positioned in the subclavian. The proximal end of the first access wire 1012 may be captured by the capture device 1032 and extracted through the third catheter 1030. In this embodiment, two separate access wires (e.g., 1012 and 1014) are not required since the proximal end of the first access wire 1012 is captured via the capture device 1032. Rather, a single access wire (e.g., first access wire 1012) may be back loaded into the second catheter 1004 and extended out of the distal end of the second catheter 1004 within the LV apex. The captured proximal end of the first access wire 1012 may then be pulled through the external wall 1011 via the third catheter 1030. This alternative embodiment uses the same access wire and only one puncture across the septum 1010. The end result is a single wire with a distal end positioned across the septum 1010 and out the venous access (e.g., jugular vein) and a proximal end that is captured in the LV apex and pulled out the external wall 1011 of the LV.

The single wire 1019 (i.e., the coupled first and second access wires, or the single wire of the alternative embodiments) may then be used to deliver the septal and epicardial anchors, 102 and 104, to the heart walls. Specifically, the epicardial anchor 104 may be positioned epicardially on the left ventricle wall and may be delivered from the left chest through the access port between the patient's ribs. The septal anchor 102 may be positioned on the right side of the interventricular septum along with the tension member 106 that joins the pair.

Figure 16:
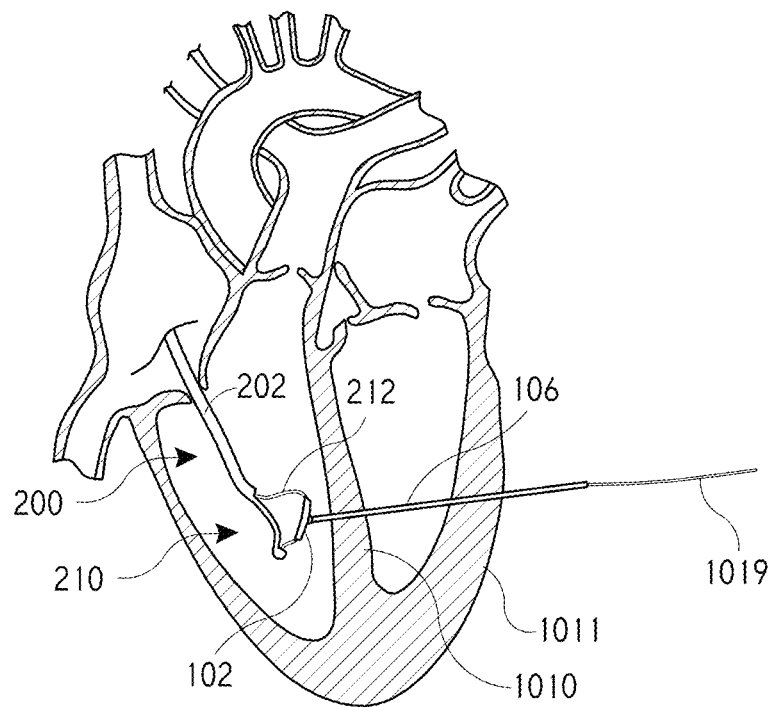

As illustrated in FIG. 16, the septal anchor 102 is delivered through the venous access (e.g., right internal jugular vein) via the septal anchor delivery device 200. The septal anchor delivery device 200 is inserted over the single access wire 1019 and through the lumen of the first catheter 1002, or another introducer, positioned within the venous access. The septal anchor 102 is advanced through the first catheter 1002 with the tension member 106 advanced distally of the septal anchor 102. The tension member 106 is passed through the penetration in the septum 1010, across the LV, and through the penetration in the external wall 1011. The tension member 106 may be pulled through the access port between the ribs externally of the patient's body. The single access wire 1019 may aid in pulling the tension member 106 through the septum 1010 and external wall 1011 and through the access port. The septal anchor 102 may then be positioned adjacent the septum 1010 by performing the first operation of the handle assembly 206, which causes the septal anchor 102 to be retractably deployed, via the cable 212, from the opening 210 of the elongate body 202.

As described herein, the septal anchor delivery device 200 may be used to ensure a proper placement of the septal anchor 102 and/or to ensure that the septal anchor 102 or tension member 106 are not entangled with tissue within the RV, such as the Chordae. For example, the RV may be imaged to ensure that the septal anchor 102 and/or tension member 106 are not entangled with tissue of the RV. If septal anchor 102 and/or tension member 106 are entangled, the septal anchor 102 and tension member 106 may be retracted within the opening 210 of the elongate body 202 via the second operation of the handle assembly 206. Entanglement of the septal anchor 102 and/or tension member 106 may be determined by inspecting the tricuspid valve and/or other areas of the heart. For example, if the tricuspid valve is not fully closing or functioning properly, the septal anchor 102 and/or tension member 106 may be entangled with heart tissue. Upon proper positioning of the septal anchor 102 and/or a determination that no entanglement has occurred, the septal anchor 102 may be permanently released from the septal anchor delivery device 200 while the tension member 106 remains positioned through the septum 1010, external wall 1011, and outside the patient's body. With the septal anchor 102 positioned against the septum 1010, only the tension member 106, which is small in caliber, penetrates through, or is positioned across, the septum 1010 and external wall 1011.

Figure 17:
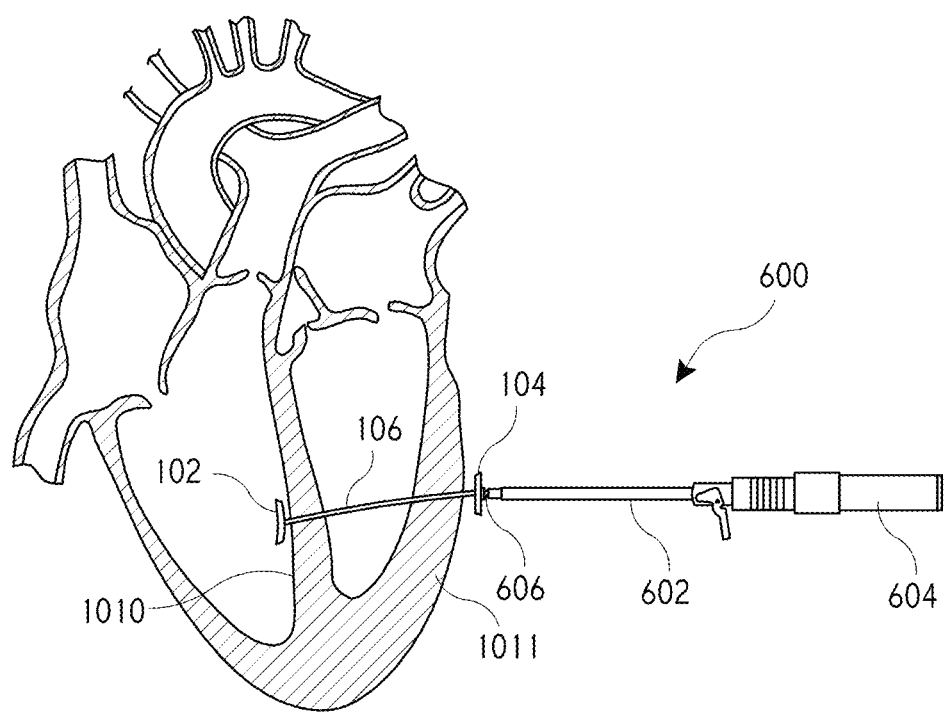

As shown in FIG. 17, with the septal anchor 102 properly positioned adjacent the septum 1010, the epicardial anchor 104 is then slidingly positioned on the tension member 106 and passed through the access port or incision in the patient's chest. In some embodiments, the epicardial anchor 104 may pivot about the tension member 106, or slide coaxially over the tether, to enable advancement of the epicardial anchor through the access port. Exemplary embodiments of such epicardial anchors are further described in the '455 and '750 patents incorporated by reference herein.

Figure 18:
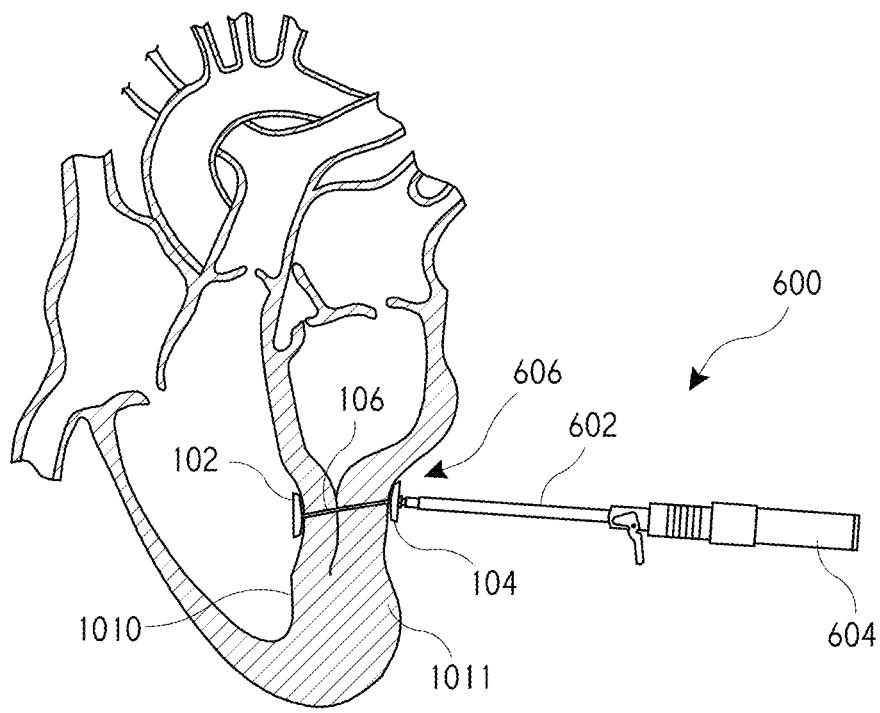

The force gauge 600 is releasably attached to the epicardial anchor 104 via the coupling mechanism 606 and used to properly position the epicardial anchor 104 against the external wall 1011. The force gauge 600 is slid over the tension member 106 by inserting the tension member 106 within the lumen of the elongate body 602. As shown in FIG. 18, with the epicardial anchor 104 positioned against the external wall 1011, the force gauge 600 is used to tension the septal and epicardial anchors, 102 and 104, in order to bring the external wall 1011 and septum 1010 into apposition with the external wall 1011 and septum 1010 touching or otherwise engaged. A desired tension force is applied, via the force gauge 600, between the septal and epicardial anchors, 102 and 104, to maintain the external wall 1011 and septum 1010 in the engaged position. The cam of the epicardial anchor's release mechanism 108 is then actuated via the force gauge 600 to lock the epicardial anchor 104 about the tension member 106 and thereby maintain the external wall 1011 and septal wall 1010 in apposition. The force gauge 600 is subsequently decoupled from the epicardial anchor 104 and removed from the patient's body. The tether cutter 700 is then used to cut the tension member 106 proximally of the epicardial anchor 104.

The above process may be repeated one or more times to deliver additional pairs of septal and epicardial anchors, 102 and 104, to desired locations of the septum 1010 and external wall 1011. For example, multiple anchor pairs may be delivered to close off a desired portion of the heart. For convenience in describing other procedures and/or referencing the above procedure elsewhere herein, the above procedure may be referred to as an RV-LV procedure since one of the anchors (i.e., the septal anchor) is deployed within the RV and the other anchor (i.e., epicardial anchor) is deployed on the LV wall. At completion of all anchor-pair placements, the septal anchors may be pulled toward the epicardial anchors, apposing the left ventricle walls and excluding a portion of the left ventricle circumference.

In addition to the RV-LV procedure, an additional anchor pair deliver procedure may involve the delivery of a pair of anchors that are both positioned on external walls of the heart (hereinafter referred to as LV-LV procedure). The pair of anchors in the LV-LV procedure are each positioned on external heart walls rather than having one anchor positioned on the septal wall within the RV. The anchor pairs are delivered distal to the apex of the RV in appropriate anatomic situations. The anchor pairs of the LV-LV procedure may partially appose the septal and LV walls along with the anchor pairs of the RV-LV procedure, thus rendering the approximate geometry of the final, reshaped apex. For example, the septal and epicardial anchors, 102 and 104, may partially appose the septum 1010 and external wall 1011 so that the septum 1010 and external wall 1011 are positioned adjacent one another without substantially contacting one another. Bringing the walls together in this manner may be performed to help hemostasis and to allow the needle 406 of the apex anchor member 400 to be easily delivered across the external walls of the heart since the distance between the external walls is decreased. The septum 1010 and external wall 1011 may be brought into full contact after performance of the LV-LV procedure.

Figure 19:
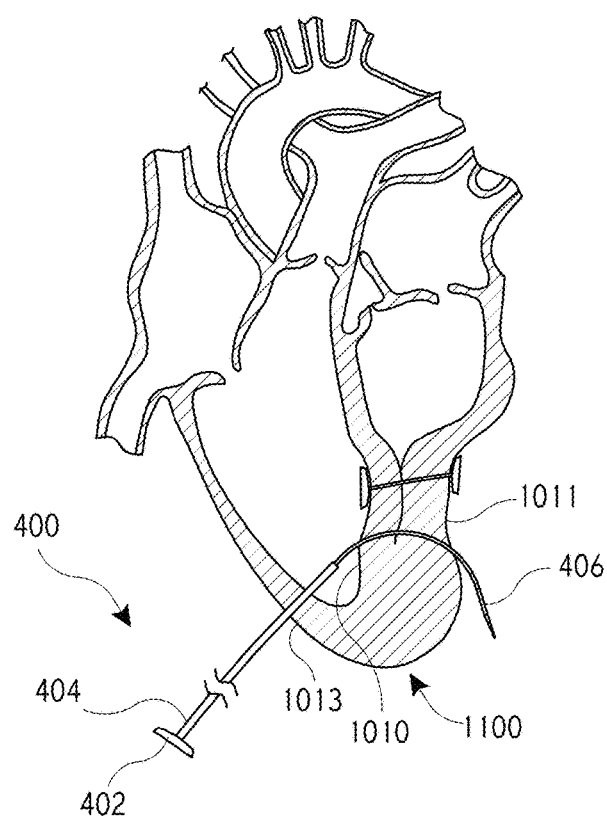

As shown in FIG. 19, to perform the LV-LV procedure in the apex of the heart, the apex anchor member 400 may be used in a surgical needle holder (not shown) to load the needle 406 such that it is positioned at about a 10-15 degree angle from the needle holder shaft. The needle 406 may then be driven across the cardiac apex through the right ventricle external wall 1013 and through the septum 1010 and left ventricle external wall 1011. The needle 406 of the apex anchor member 400 is retrieved such as by grasping the needle 406 with a forcep or surgical instrument (e.g., right angle clamp) and pulling the needle 406 distally of the left ventricle external wall 1011. The needle 406 of the apex anchor member 400 is pulled through the port or incision in the patient's chest and outside the patient's body, which causes the elongate tension member 404 and the pivoting anchor 402 that is attached to the distal end of the tension member 404 to be pulled into contact with the right ventricle external wall 1013. The pivoting anchor 402 may be pulled toward the right ventricle external wall 1013 in a low profile configuration with the anchor 403 axially aligned with the tension member 404. The anchor 402 may then be pivoted into a deployed configuration with the anchor 402 roughly orthogonal to the tension member 404.

After the pivoting anchor 402 is positioned against the right ventricle external wall 1013, an epicardial anchor 104 is then positioned over the elongate tension member 404 and slid into contact with the left ventricle external wall 1011.

Figure 20:
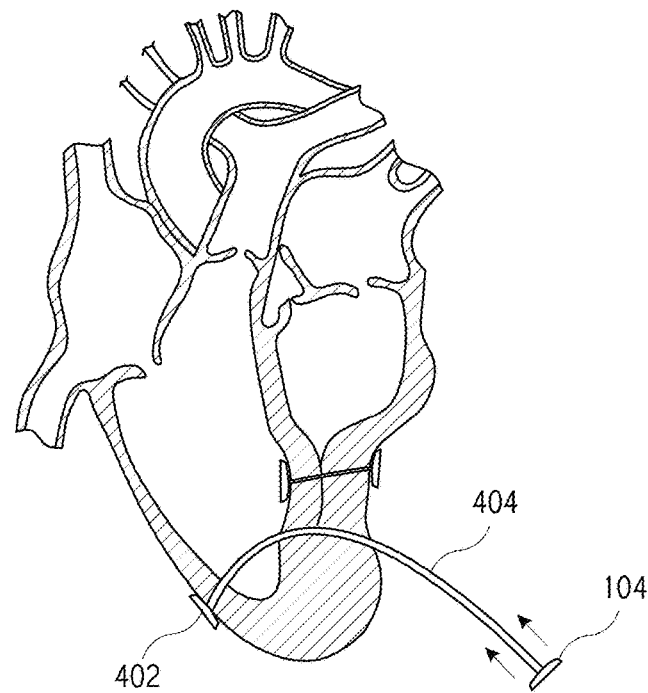
Figure 21:
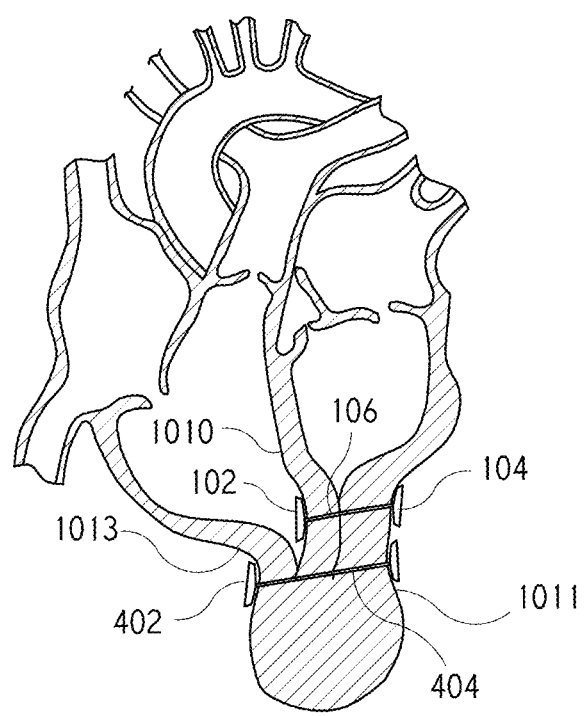

FIG. 20 illustrates the epicardial anchor 104 positioned about the elongate tension member 404 and being slid toward the left ventricle external wall 1011. The force gauge 600 may be used to engage the epicardial anchor 104 with the left ventricle external wall 1011 and to apply tension to the pivoting anchor 402 and epicardial anchor 104 as described herein. FIG. 21 illustrates multiple anchor pairs being employed to reconfigure the geometry of the heart and to close of a lower portion of the left ventricle.

The positioning of each of the anchors may be checked via fluoroscopically. As described in the '711 patent and/or the '556 application, the external wall 1011 and septum 1010 may be apposed and tensioned to a desired force (e.g., 2-3 Newtons) using the force gauge 600. Each of the tension members may then be cut via the tether cutter 700.

An advantage of the above process is that the delivery of the septal and epicardial anchors, 102 and 104, does not require major incisions in the patient's body and/or heart tissue. Rather, the process may be performed entirely via a percutaneous approach. The "percutaneous approach" means that the catheters are routed through the vasculature and are positioned within the RV and LV rather than having one of the catheters positioned on the exterior of the heart. Routing the catheters through the vasculature minimizes the incisions that need to be made in the patient's body, which minimizes the trauma and risks associated therewith, such as infection, recovery time, and the like. For example, the process may only involve the access port positioned between the patient's ribs, a venous access for the first catheter 1002, and an arterial access for the second catheter 1004. As such, hemorrhaging is greatly minimized as are any scars associated with the procedure. In addition, routing the catheters through the vasculature may reduce the involvement of a surgeon.

An additional advantage is that the delivery of the access wire(s) (i.e., for subsequent placement of the septal and epicardial anchors) occurs entirely within the heart rather than having one or more procedures performed externally of the heart. Specifically, the first catheter 1002 positioned within the RV and the second catheter 1004 positioned within the LV are sufficient to deliver the access wire(s) through the septal and LV walls. Since the process may occur entirely within the heart, larger holes, punctures, or penetrations through the heart walls may be avoided. Rather, the only hole or penetration through the heart walls (i.e., septum, LV wall, or other walls), prior to delivery of the heart anchors, may be the extremely small access wire, which in some embodiments may have a diameter of 0.014", or the trans-septal needle. The penetration or incision in the heart wall is significantly smaller than those that result from conventional procedures where an external catheter is delivered through the external wall and/or septal wall. The elimination or reduction of larger penetrations through the heart walls helps facilitate patient recovery, hemostasis, and/or other issues. In addition, delivery of the guidewire/access wire internally rather than externally reduces the risk of infection since exposure to external objects that may carry pathogens is greatly reduced.

Delivering the guidewire/access wire internally from the LV further reduces complications with the perforations or penetrations through heart walls. For example, delivering the guidewire/access wire through the septum and external walls from within the LV ensures that the penetration through the heart is greatly reduced since the guidewire/access wire or trans-septal needle is the only component that punctures and is advanced through these walls. Conventional procedures typically require that the catheter be inserted or advanced through the heart wall, which results in a significantly larger incision or hole in the heart wall. The smaller hole or incision in the heart wall that is achieved via advancing the guidewire/access wire through said walls from within the LV results in the incision or hole being substantially the same size as the guidewire/access wire, which greatly minimizes hemorrhaging and helps ensure that the tissue that contacts the septal and epicardial anchors is not substantially weakened due to the hole or incision.

Study

A series of studies were conducted using the procedures and tools described above. The studies were conducted to deliver a 0.014" guidewire across the left ventricle, septum, and right ventricle in acute porcine and ovine models. Fully mature porcine (pigs) and ovine (sheep) were used in these studies as pigs and sheep have hearts that are similar in size and structure as humans. The pig and sheep hearts also lack the extensive collateral coronary circulation of other large animals, making the model more reliable.

The animals were prepared for the procedure following general endotracheal anesthesia, insertion of standard I.V., and arterial monitoring lines. The animals were positioned supine. All I.V. and monitoring lines were placed in the left side of the neck. A small left thoracotomy incision was made at approximately the 4th intercostal space. The animal were heparinized to an ACT>250 sec. When required, a small rib re-tractor was used for access to the left ventricle. A percutaneous puncture (or small cut down) was made over the right external jugular vein for right-sided tool access. A percutaneous puncture (or small cut down) was made over the left carotid for trans-septal needle tool access.

In each animal, an LV-LV anchor and one or more RV-LV anchors were deployed using process similar to the LV-LV procedure and RV-LV procedure described above. A location site for the LV-LV anchor was first selected. Using surgical instruments such as needle drivers, the LV apex anchor member was inserted through the back of the heart, aiming for the epicardial LV-LV site using fluoroscopic guidance. Once the needle tip of the LV apex anchor member was visible on the other side of the LV wall, the needle was pulled through the LV wall using a surgical instrument, which pulled the tether through both walls of the heart. A septal anchor attached to the distal end of the LV apex anchor member' tether was positioned adjacent the right wall of the apex and rotated to an optimal position. The tether was cut just below the connection between the tether and needle. An epicardial anchor was then advanced over the tether using the epicardial anchor delivery device.

Using the LV-LV anchor pair as a marker, a 6 or 7 Fr introducer catheter was placed in the second anchor site, using a needle and guidewire. A 14 Fr introducer catheter was inserted into the right external jugular vein using a 14 Fr dilator catheter. A Swan-Ganz catheter was used to deliver two 0.025" guide wires into the right ventricular outflow tract/pulmonary artery. The Swan Ganz catheter was removed leaving the wires in place, one as a "septum marker" and the other as the "working" wire.

A snare, such as a GooseNeck® snare, was then delivered along the RV septum to serve as a target for the trans-septal needle. To deliver the snare, a steerable introducer catheter and snare sheath were delivered over the "working" wire, and positioned along the RV septum. The working wire was then removed and the snare was inserted through the snare sheath and positioned in place. The steerable introducer catheter was used to manipulate the snare into an optimal location.

A second 14 Fr introducer catheter was then inserted into the Carotid Artery. A second catheter was preloaded with 0.014" guide wire and a pigtail catheter. The second catheter was inserted through a lumen of the second 14 Fr introducer catheter and the aortic valve was crossed using the pigtail catheter. The second catheter was positioned in or near the LV apex.

An LV angiogram was performed to determine the LV chamber and septal anatomy. The second catheter was advanced in the apical region and the pigtail catheter was removed. A 0.014" guidewire was then delivered into the LV and captured by the snare positioned in the RV. To deliver the guidewire, a trans-septal needle was inserted through the second catheter and positioned towards the septum adjacent the location of the snare positioned in the RV. The trans-septal needle was then used to puncture the septal wall and the guidewire was inserted through the trans-septal needle and into the snare located in the right ventricle. The snare device was actuated to capture the guidewire and the guidewire and snare were retracted into the introducer catheter located in the jugular vein.

A second snare device was then inserted through the second introducer catheter positioned through the carotid artery. The second snare device was positioned in the left ventricle adjacent a desired target site. An opposite end of the 0.014" guidewire was inserted into the second catheter positioned in the LV. The guidewire was then positioned adjacent the second snare and the LV wall was punctured so that the guidewire could access the second snare. The second snare was actuated to capture the guidewire and the second snare and guidewire were retracted through the small introducer. After this procedure, the guidewire extended through the jugular vein, the RV, the septal wall, the LV, the LV wall, and through the thoracotomy incision.

A septal anchor and epicardial anchor were then delivered to the septal and LV walls, respectively. Specifically, from the Jugular side, the septal anchor assembly was advanced along the guidewire and into the RV via the septal anchor delivery device. The tether attached to the septal anchor was advanced over the guidewire and through the septum and LV walls. The septal anchor was positioned against the septum after confirmation by fluoroscopy and using the septal anchor delivery device. The epicardial anchor was placed over tether and onto the LV epicardial surface using the epicardial anchor delivery device and/or force gauge. Depending on the size of the heart, multiple RV-LV anchors were placed using the procedure described above.

Study Results

Figure 22:
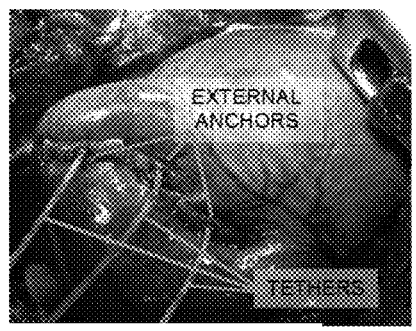
FIGS. 22-41 illustrate images taken after delivery of multiple anchor pairs within a specimen in accordance with the treatment procedures described herein.
Figure 23:
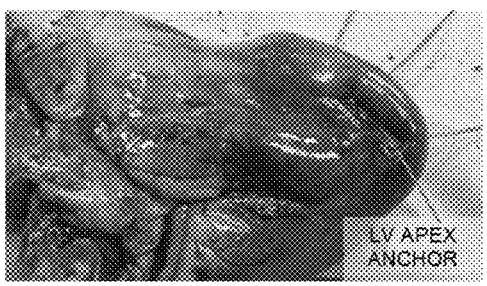
Figure 24:

Described below are the results of the above procedure on various animals. FIGS. 22-24 are images taken after the delivery of anchor pairs in a first pig. Specifically, three septal and epicardial anchor pairs (two RV-LV sites and one LV-LV site) were delivered per the procedure listed above. Anchor placement was slightly posterior but plication still showed significant reduction in LV size. FIGS. 42-45 are fluoroscopic images taken during the study of the first pig.

Figure 25:
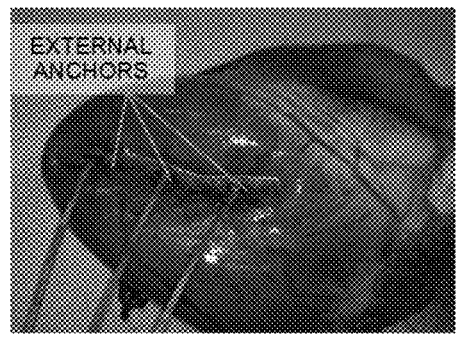
Figure 26:
Figure 27:
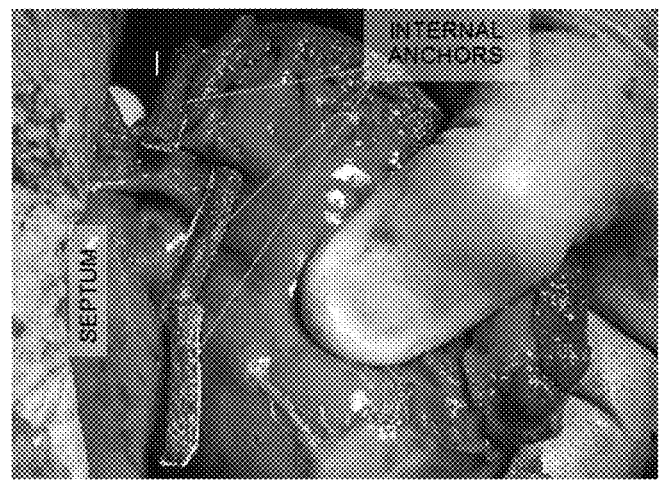
Figure 28:
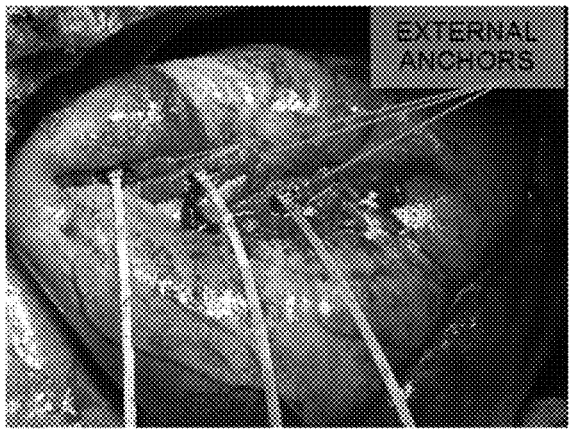
Figure 29:
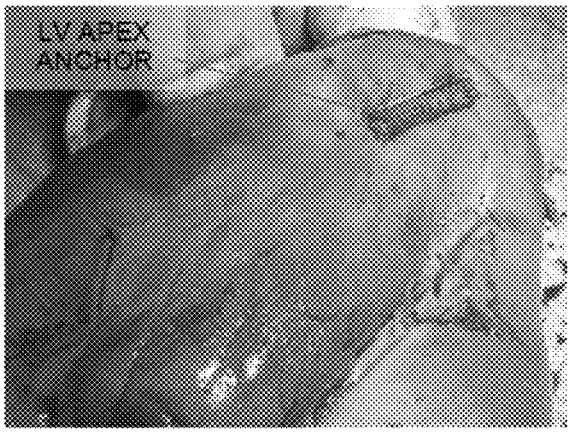
Figure 30:
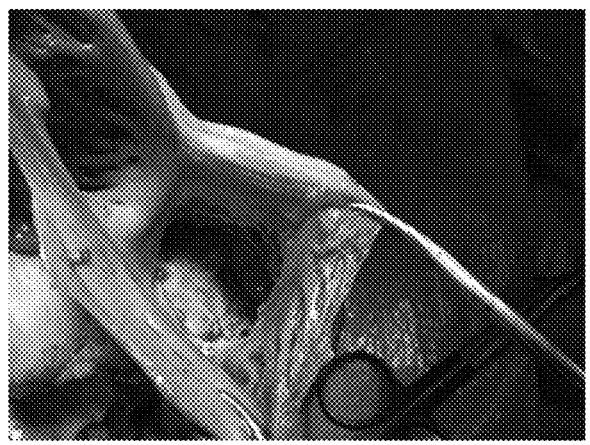
Figure 31:
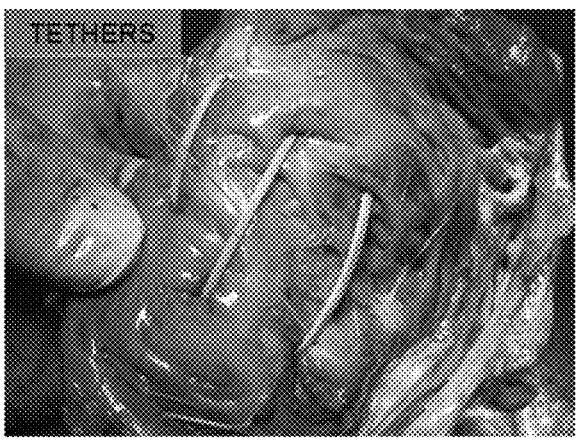

FIGS. 25-27 are images taken after the delivery of anchor pairs in a second pig. Three septal and epicardial anchor pairs (two RV-LV sites and one LV-LV site) were delivered per the procedure listed above. Anchor placement and LV reduction after plication were ideal. FIGS. 46-49 are fluoroscopic images taken during the study of the second pig.

FIGS. 28-31 are images taken after the delivery of anchor pairs in a third pig. Three septal and epicardial anchor pairs (two RV-LV sites and one LV-LV site) were delivered per the procedure listed above. The myocardial infarction was induced by ethanol. Anchor placement was slightly posterior but there was no interference between the anchors and the RV chordae/trabeculae. FIGS. 50-53 are fluoroscopic images taken during the study of the third pig.

Figure 32:
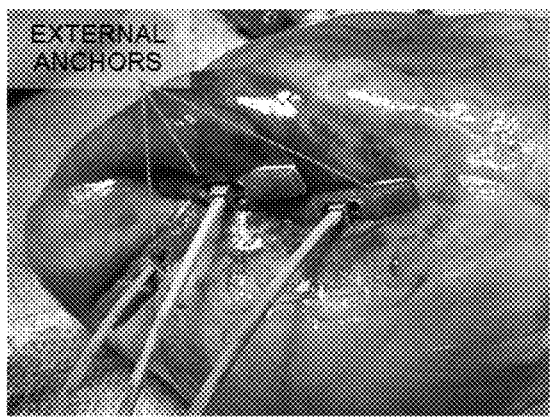
Figure 33:
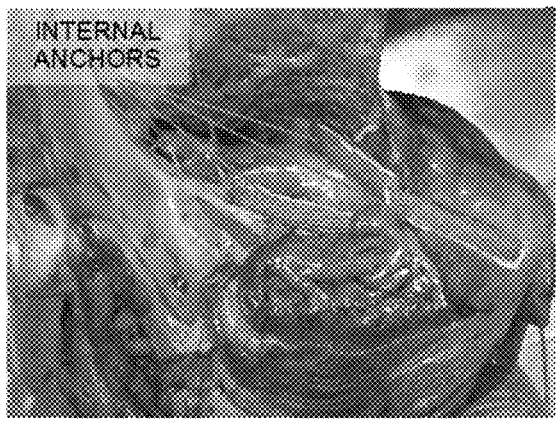
Figure 34:
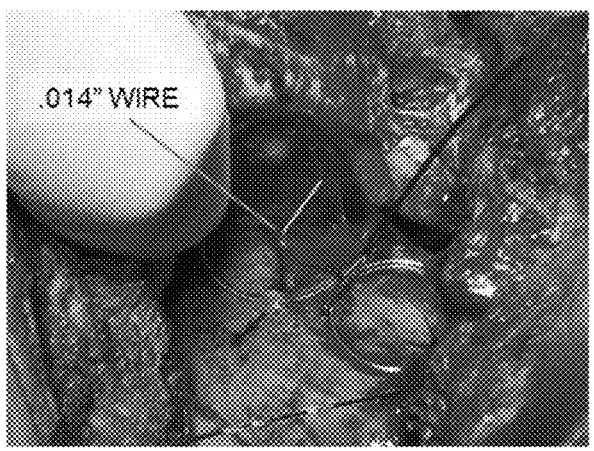

FIGS. 32 and 33 are images taken after the delivery of anchor pairs in a fourth pig. Three septal and epicardial anchors pairs (two RV-LV sites and one LV-LV site) were delivered per the procedure listed above, except for the lower or apical-most LV-RV anchor. In delivering this LV-RV anchor, a Swan-Ganz catheter was used inside an Agilis steerable catheter to deliver the guide wire across the septum instead of using the trans-septal needle. The myocardial infarction was induced by ethanol. FIGS. 54-57 are fluoroscopic images taken during the study of the fourth pig.

Figure 35:
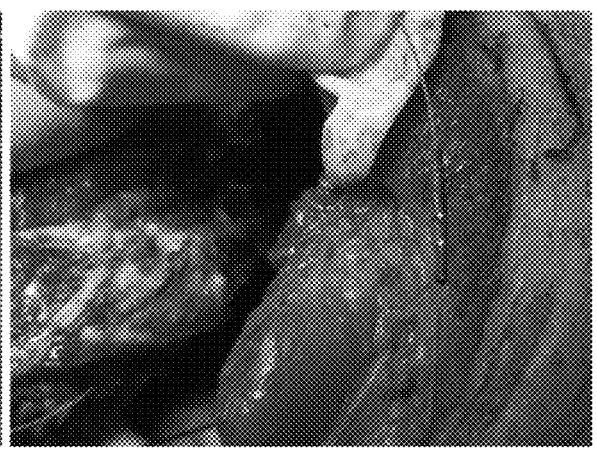
Figure 36:
Figure 37:
Figure 38:
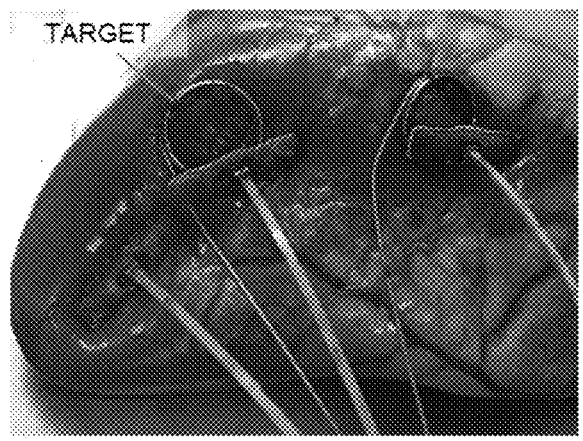
Figure 39:
Figure 40:
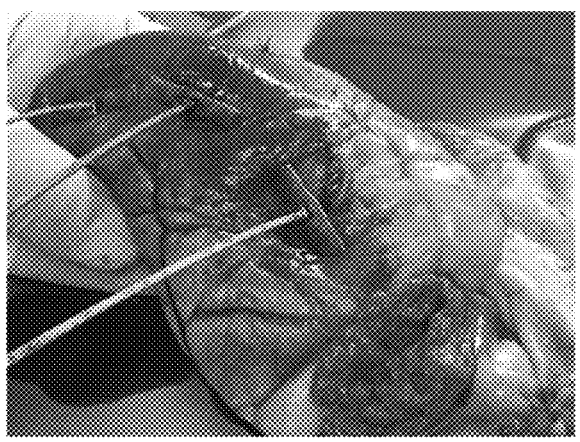
Figure 41:
Figure 42:
Figure 43:
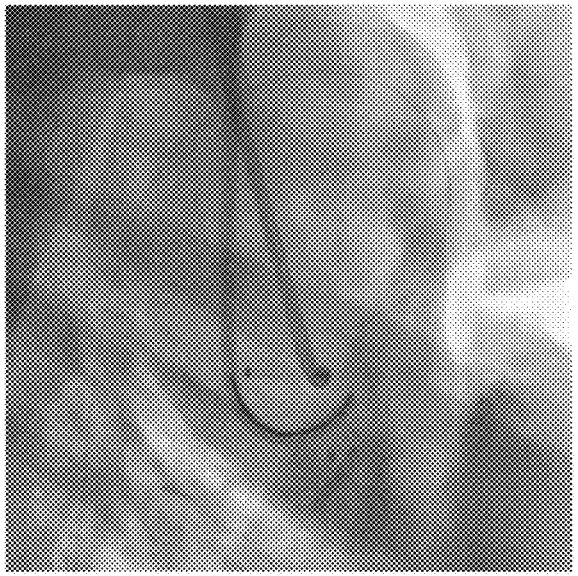
Figure 44:
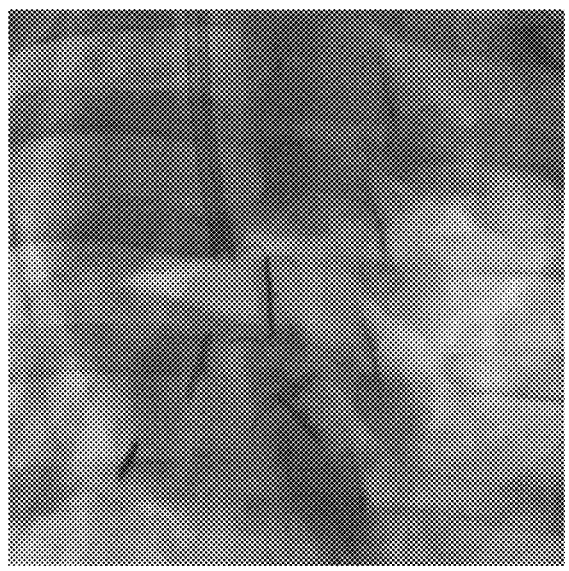
Figure 45:
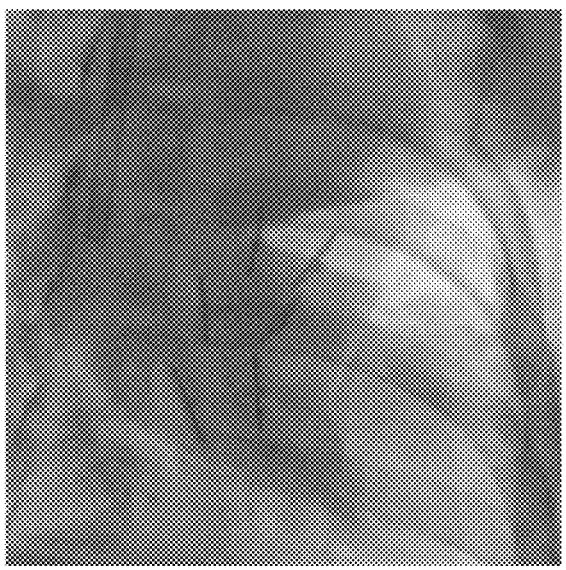
Figure 46:
Figure 47:
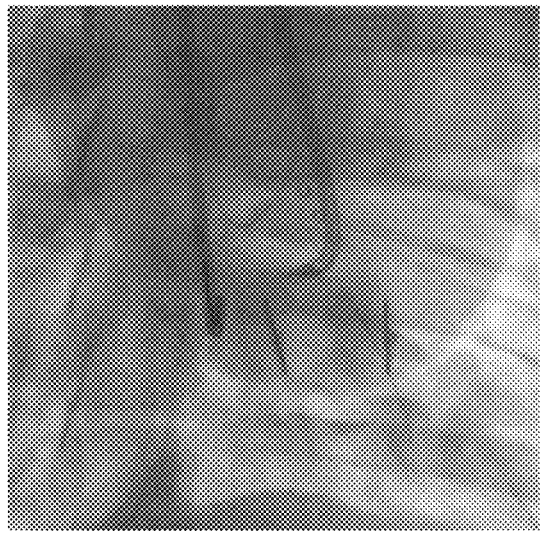
Figure 48:
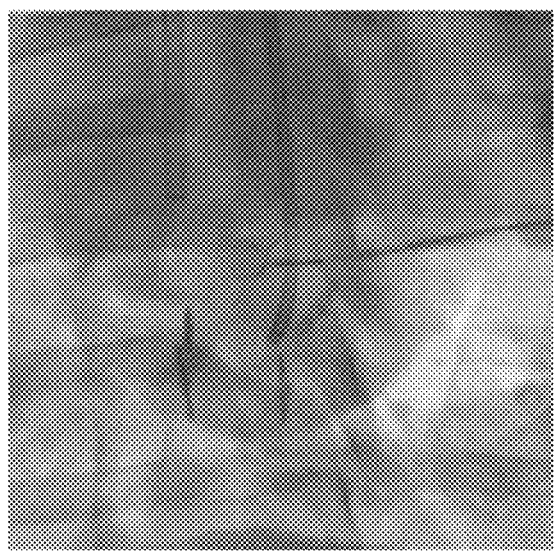
Figure 49:
Figure 50:
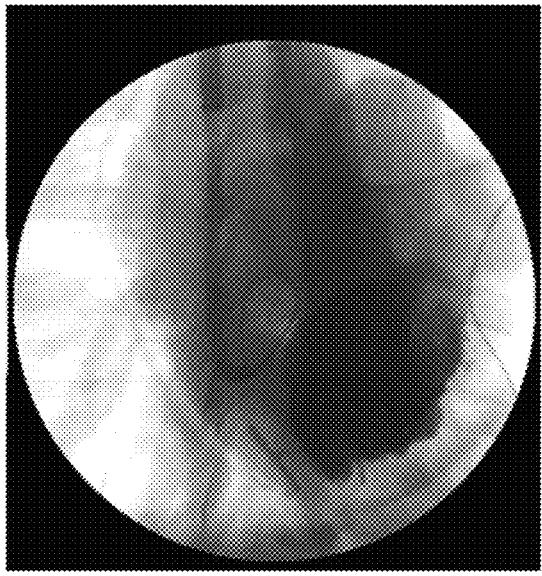
Figure 51:
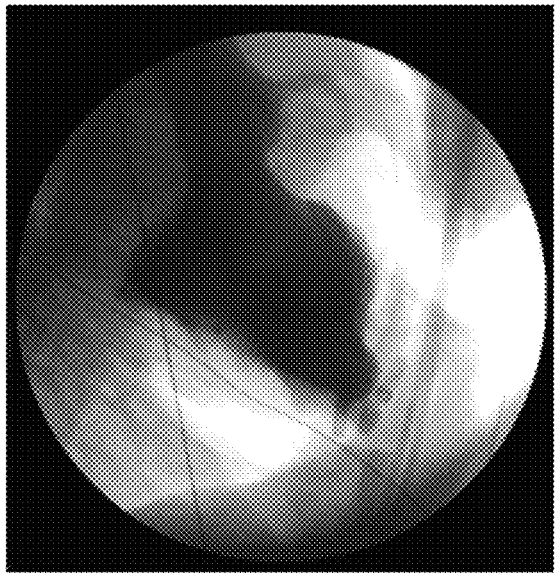
Figure 52:
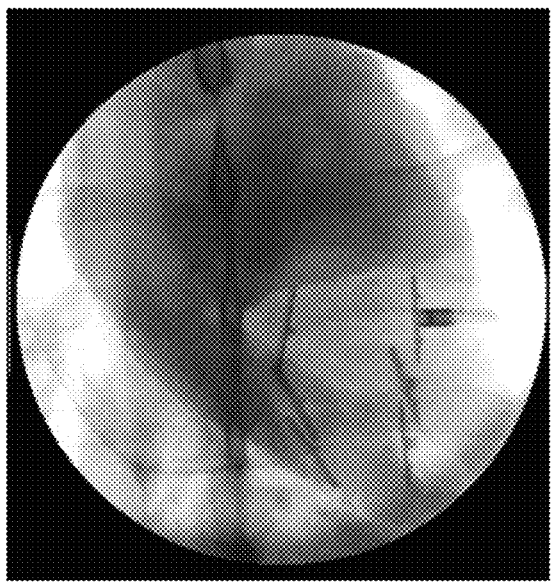
Figure 53:
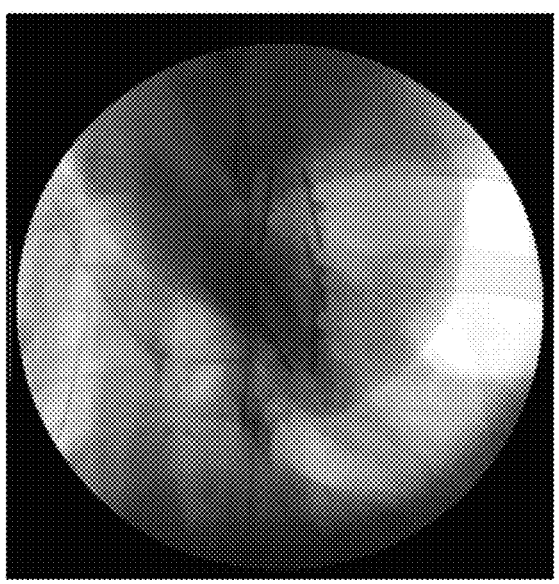
Figure 54:
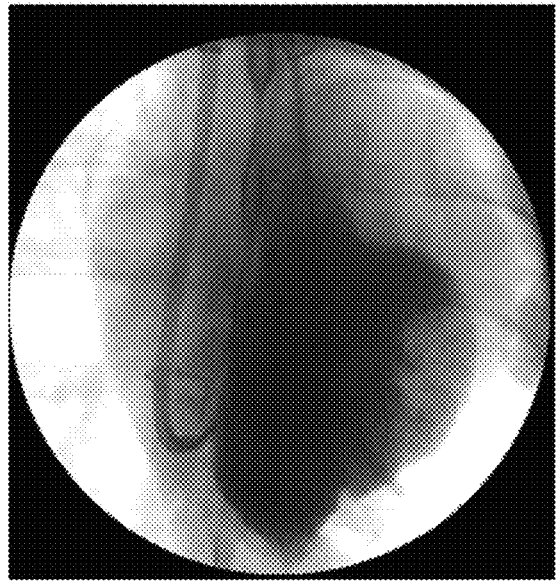
Figure 55:
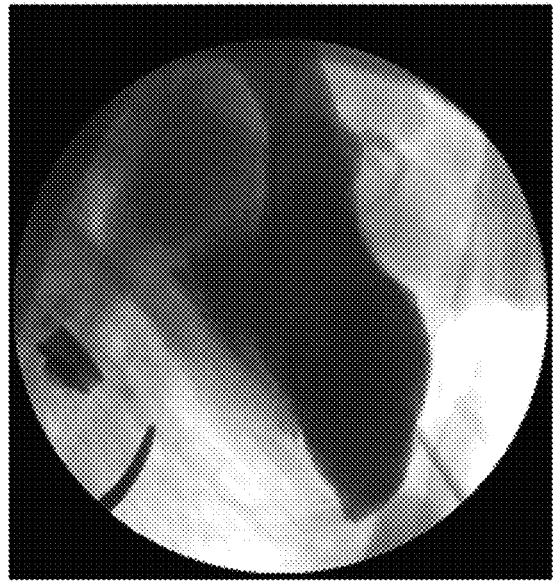
Figure 56:
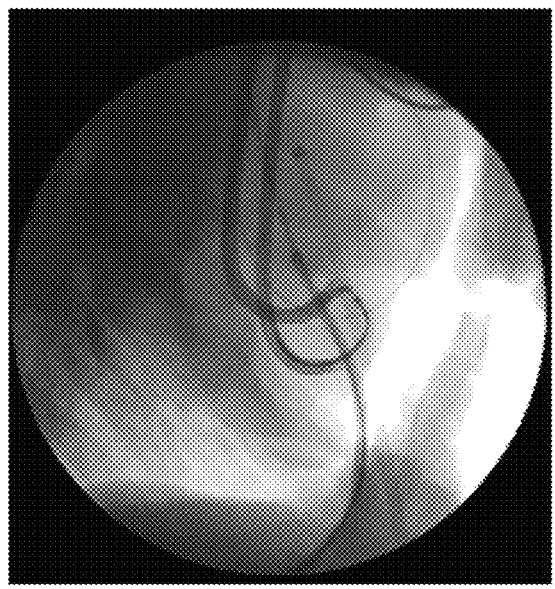
Figure 57:
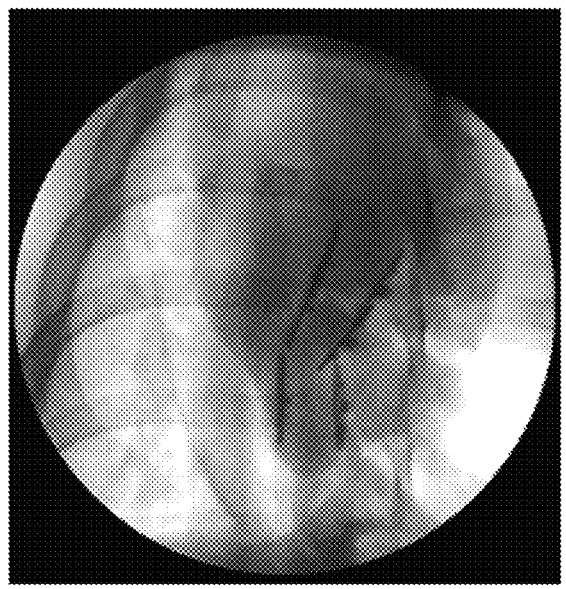
Figure 58:
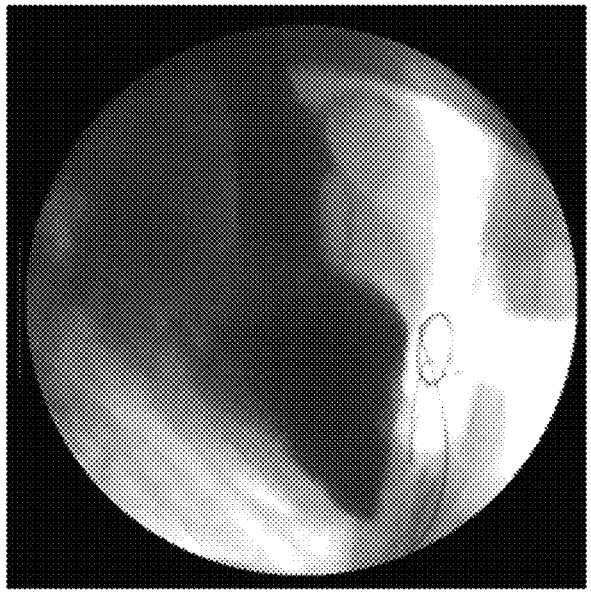
Figure 59:
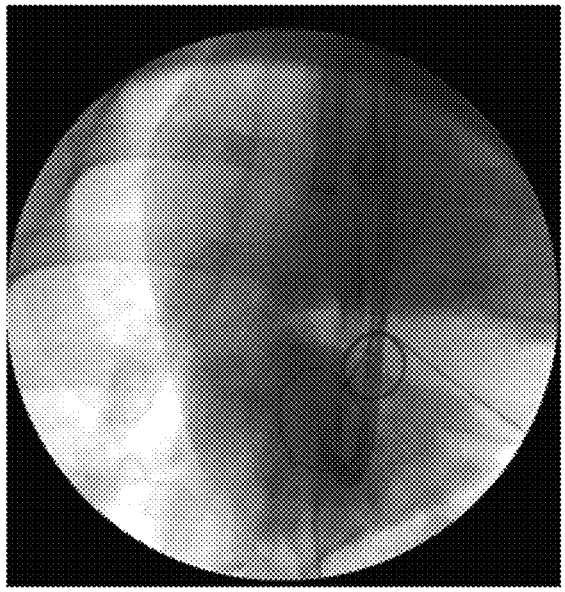
Figure 60:
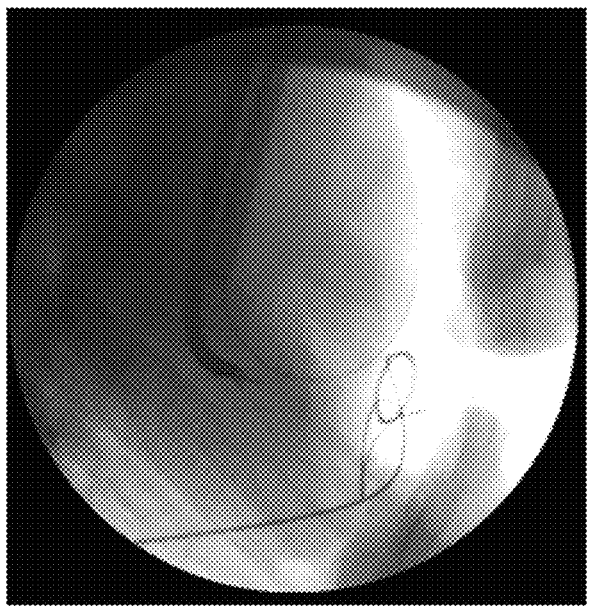
Figure 61:
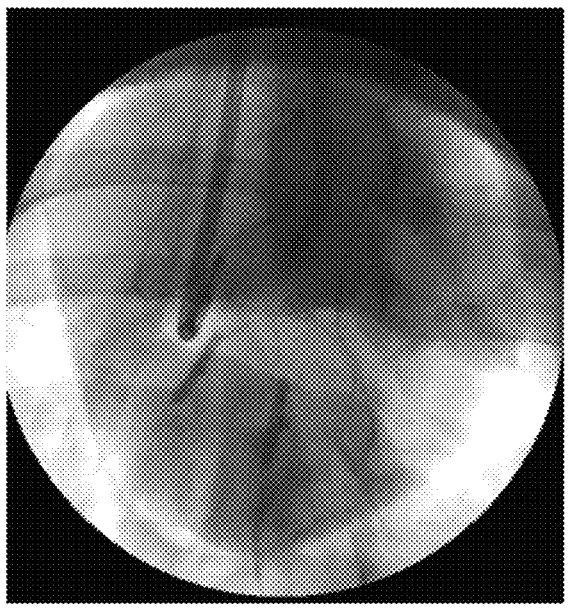
Figure 62:
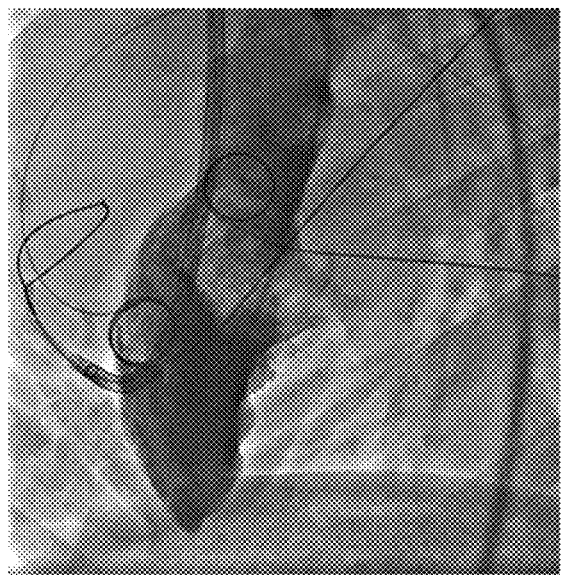
Figure 63:
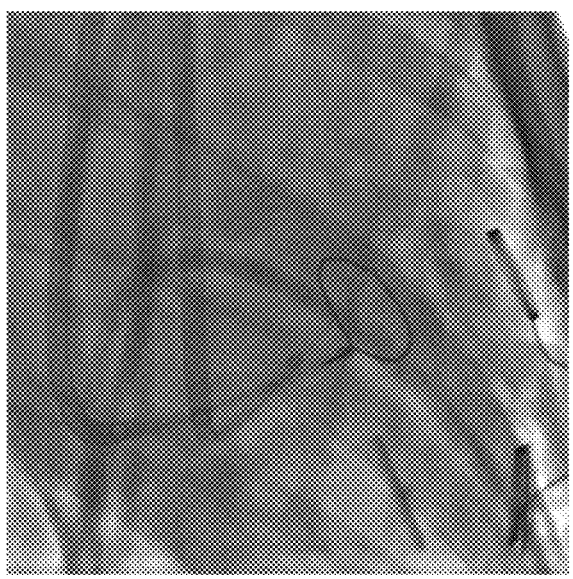
Figure 64:
Figure 65:
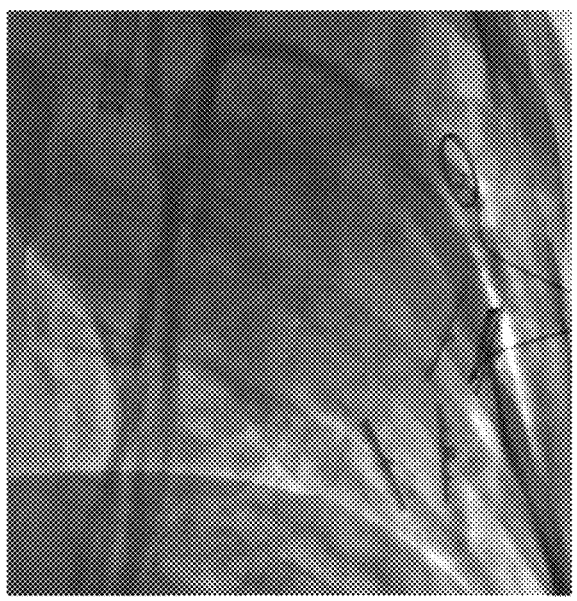

FIGS. 34-37 are images taken after the delivery of anchor pairs in a fifth pig. Three septal and epicardial anchor pairs (two RV-LV sites and one LV-LV site) were delivered per a similar yet modified procedure. Specifically, in crossing the septum, an electro cauterization device was used to apply a short burst of RF energy (less than 20 watts) to the guidewire to help advance it through the scar. In addition, instead of using the 7 Fr introducer catheter to snare the arterial guidewire in the LV, the trans-septal needle was used to pass a second 0.014" guidewire out through the free LV epicardial wall into targets placed on the outside of the epicardial surface of the left ventricle. The guidewire was then grasped and pulled through the incision. Therefore, two wires are placed using the carotid artery access. The second wire was then attached to the wire previously passed through the septum by crimping a small section of tubing over each end of wire as illustrated in FIG. 35. The attachment was between the two wire ends outside the arterial 14 Fr introducer catheter. The epicardial wire was then pulled or tensioned, passing the crimped tube through the arterial 14 Fr introducer catheter and out through the LV wall though the incision. Once the crimped tube was grasped, the wire and crimped tube section was cut away, leaving a trans-septal wire from the jugular vein crossing the septum and outside the LV epicardial surface. FIGS. 58-61 are fluoroscopic images taken during the study of the fifth pig.

FIGS. 38-41 are images taken after the delivery of anchor pairs in a sheep. Three septal and epicardial anchor pairs (two RV-LV sites and one LV-LV site) were delivered per a similar yet modified procedure. The sheep was used to test the wire placement from the carotid artery outside the LV epicardium and to test wire placement from the carotid artery across the septum into a snare positioned within the RV. Both wire placements were done without using the trans-septal needle and instead utilized the snare sheath to support the wire crossing. The wire crimping method was also used. FIGS. 62-65 are fluoroscopic images taken during the study of the sheep.

Figure 66:
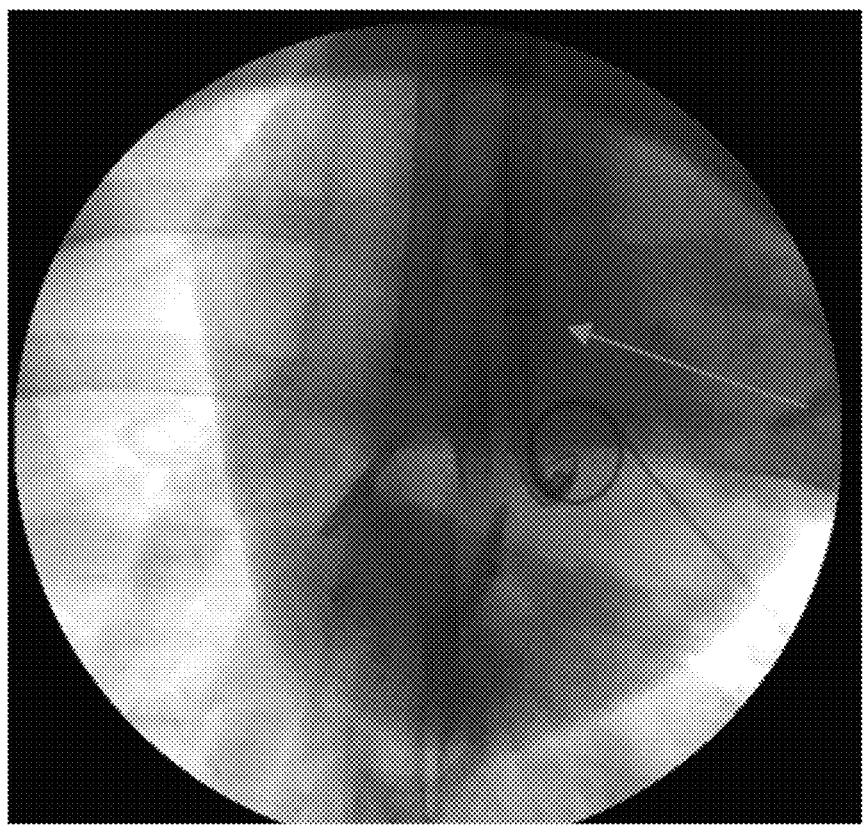
FIG. 66 illustrates a 14 Fr introducer catheter inside a left ventricle.

In many of the above test procedures that were performed, the arterial 14 Fr introducer catheter was advanced past the aortic valve into the left side of the heart. The goal of this step was to protect the aortic valve from damage by the 0.014" guidewire. While it was determined to be possible to advance the distal end of the introducer catheter past the aortic valve, it was also determined to be unnecessary. The 0.014" guidewire remains inside the arterial steerable catheter, which serves as the shield for the aortic valve and replaces the introducer catheter as the protective device. FIG. 66 illustrates the 14 Fr introducer catheter inside the left ventricle.

Study Conclusion

The trans-septal needle was able to be inserted within the Agilis steerable catheter and track inside the catheter. The trans-septal needle was long enough to reach the septum for all 4 animals at both the apical and basal locations along the LV septum. The 0.014" guidewire was easily inserted within the trans-septal needle and was able to traverse the LV septum, both scarred tissue and healthy tissue. The trans-septal needle was durable and maintained functional integrity during multiple guidewire crossings and multiple procedures. The trans-septal needle did not interfere with imaging components. The trans-septal needle was visible with fluoroscopy. A 0.014" guidewire was easily inserted within the trans-septal needle within a steerable catheter within the carotid artery and was able to traverse the LV epicardial surface, both scarred tissue and healthy tissue. The ability to cross the septum can be done without the trans-septal needle. A steerable catheter and a support catheter such as the snare sheath is enough support to allow the guidewire to cross the septum. The ability to penetrate both scarred and healthy tissue with a guidewire from an arterial access is possible without the trans-septal needle. A steerable catheter and a support catheter such as the snare sheath is enough support to get a guidewire to penetrate the LV epicardium. The procedure was possible in both the porcine and ovine model. The animal models in this study had a heart similar in structure as humans. The new LV approach and devices were able to successfully deploy a 0.014" guidewire at each anchor location for each animal.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard to an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method for treating a heart within a patient, the heart having first and second chambers with a septum there between, the second chamber having an exterior wall, the method comprising:
    advancing an elongate shaft from outside the patient and through the vasculature so that a distal end of the elongate shaft is disposed in the second chamber, the elongate shaft having a proximal end and a lumen that extends between the proximal end and the distal end;
    positioning the distal end of the elongate shaft adjacent the septum;
    penetrating the septum and delivering a first guidewire from within the lumen of the elongate shaft and across the septum so that a distal end of the first guidewire is positioned in the first chamber and is extractable therefrom;
    subsequent to penetrating the septum, repositioning the distal end of the elongate shaft within the second chamber so that the distal end of the elongate shaft is adjacent the external wall;
    penetrating the external wall and delivering a second guidewire from within the lumen of the elongate shaft and across the external wall so that a distal end of the second guidewire is positioned outside the external wall and is extractable therefrom;
    while a portion of the first guidewire and a portion of the second guidewire are positioned within the first chamber, coupling the first guidewire to the second guidewire outside of a body of the patient so that the first guidewire is locked relative to the second guidewire outside the body; and
    delivering a coupled end of the first guidewire and the second guidewire through the lumen of the elongate shaft to join a path within the second chamber that extends between the penetration of the septum and the penetration of the external wall.

2. The method of claim 1, wherein the elongate shaft comprises a needle that is disposed within the lumen of the elongate shaft, the needle being deliverable from within the lumen of the elongate shaft to penetrate the septum and to penetrate the external wall.

3. The method of claim 1, wherein the first guidewire is advanced from within the lumen of the elongate shaft to penetrate the septum and wherein the second guidewire is advanced from within the lumen of the elongate shaft to penetrate the external wall.

4. The method of claim 1, further comprising:
    advancing an additional elongate shaft from outside the heart and through the vasculature into the first chamber so that a distal end of the additional elongate shaft is disposed in the first chamber; and coupling, within the first chamber of the heart, the distal end of the additional elongate shaft with the distal end of the first guidewire so as to join a path of the first guidewire with a path of the additional elongate shaft, the additional elongate shaft having a flexible body that is slidably coupled to the additional elongate shaft and that is configured for in situ coupling with the distal end of the first guidewire.

5. The method of claim 4, wherein the flexible body is a snare device that is slidably disposed within a lumen of the additional elongate shaft and that is axially advanceable therefrom, the snare device having an opening configured for capturing the first guidewire within the first chamber, the snare device being biased to expand from a low profile configuration when released in the first chamber so as to expand the opening.

6. The method of claim 4, further comprising:
advancing an external elongate shaft from outside the patient to the external wall of the second chamber so that a distal end of the external elongate shaft is disposed adjacent the external wall; and coupling the external elongate shaft with the distal end of the second guidewire for extracting the second guidewire from the external wall to outside the patient body.

7. The method of claim 6, wherein the external elongate shaft comprises a second snare device that is slidably disposed within a lumen of the external elongate shaft and that is axially extendable therefrom, the second snare device being positionable on the external wall of the second chamber for coupling with the second guidewire.

8. The method of claim 1, further comprising:
advancing a first anchor from outside the heart along the joined path of the first guidewire and the second guidewire so that the first anchor is positioned against the septum within the first chamber, the first anchor being coupled with a tension member that extends from the first anchor, through the septum, through the second chamber, and through the external wall when the first anchor is positioned against the septum;

advancing a second anchor from outside the heart along the tension member so that the second anchor is positioned against the external wall, the second anchor being slidably coupled with the tension member; and applying tension between the first anchor and the second anchor via the tension member in order to urge the septum and the external wall to engage.

9. The method of claim 8, wherein the first anchor is advanced from outside the heart via an alignment device that includes: an elongate body, an opening in a distal end of the elongate body within which the first anchor is positioned; and a reposition mechanism; and wherein the method further comprises:

advancing the distal end of the alignment device within the first chamber; and deploying, via the reposition mechanism, the first anchor from the opening of the elongate body to align the first anchor with the septum within the first chamber, the first anchor being retractable within the opening of the elongate body via the reposition mechanism in order to reposition the first anchor about the septum.

10. The method of claim 9, wherein the reposition mechanism includes a guidewire or cable that is slidably disposed within a lumen of the elongate body and within an axial lumen of the first anchor, the elongate body being configured such that distal sliding of the guidewire or cable within the lumen of the elongate body causes a portion of the guidewire or cable to protrude outwardly from the opening of the elongate body thereby causing the first anchor to be retractably deployed from the opening.

11. The method of claim 1, further comprising securing a coupling member to a proximal end of the first guidewire and a proximal end of the second guidewire to couple the first guidewire to the second guidewire.

12. The method of claim 1, further comprising:
penetrating external walls of an apex of the heart via a needle of an apical anchor device, the apical anchor device comprising an elongate tension member having an anchor attached to a proximal end and the needle attached to a distal end; and pulling the needle through the external walls of the apex of the heart so as to advance the anchor, via the elongate tension member, into engagement with one of the external walls of the apex.

13. The method of claim 12, wherein the needle has a curved or arcuate configuration and wherein the needle is made of a more rigid material than the elongate tension member.

14. The method of claim 13, wherein the anchor of the apical anchor device is pivotably coupled to the proximal end of the elongate tension member such that the anchor is pivotable from a low-profile configuration to a deployed configuration.

15. A method for treating a heart within a patient, the heart having first and second chambers with a septum there between, the second chamber having an exterior wall, the method comprising:

advancing a first elongate shaft from outside the patient and through the vasculature so that a distal end of the first elongate shaft is disposed in the first chamber;

advancing a second elongate shaft from outside the heart and through the vasculature into the second chamber so that a distal end of the second elongate shaft is disposed in the second chamber, the second elongate shaft having a proximal end and a lumen that extends between the proximal end and the distal end;

positioning the distal end of the second elongate shaft adjacent the septum;

penetrating the septum;

delivering a first guidewire from within the lumen of the second elongate shaft and across the septum so that a distal end of the first guidewire is positioned in the first chamber and is extractable therefrom;

coupling, within the first chamber of the heart, the distal end of the first elongate shaft with the distal end of the first guidewire so that the first guidewire is extractable from the first chamber via the first elongate shaft;

extracting the distal end of the first guidewire from the first chamber and through the vasculature toward a first location outside the patient body;

repositioning the distal end of the second elongate shaft within the second chamber so that the distal end of the second elongate shaft is adjacent the external wall;

penetrating the external wall;

delivering a second guidewire from within the lumen of the second elongate shaft and across the external wall so that a distal end of the second guidewire is positioned outside the external wall and is extractable therefrom to outside the patient body;

extracting the distal end of the second guidewire from the external wall toward a second location outside the patient body;

coupling the first guidewire to the second guidewire to form a path that extends from outside the patient body at the first location, into the first chamber, through the septum, through the second chamber, through the external wall, and outside the patient body at the second location;

delivering a coupled end of the first guidewire and the second guidewire through the lumen of the second elongate shaft into the second chamber; and extracting the coupled end of the first guidewire and the second guidewire from within the body so that a solitary or unitary guidewire extends through the septum, through the second chamber, through the external wall.

16. The method of claim 15, further comprising:

advancing a first anchor from outside the patient body at the first location along the formed path so that the first anchor is positioned against the septum within the first chamber, the first anchor being coupled with a tension member that extends from the first anchor, through the septum, through the second chamber, and through the external wall when the first anchor is positioned against the septum;

slidably coupling a second anchor with the tension member;

advancing the second anchor along the tension member from outside the patient body at the second location so that the second anchor is positioned against the external wall; and applying tension between the first anchor and the second anchor via the tension member in order to urge the septum and the external wall into engagement.

17. The method of claim 15, further comprising securing a coupling member to a proximal end of the first guidewire and a proximal end of the second guidewire to couple the first guidewire to the second guidewire.

18. The method of claim 15, wherein penetrating the septum comprises advancing a needle from within the lumen of the second elongate shaft and through the septum and wherein penetrating the external wall comprises advancing the needle from within the lumen of the second elongate shaft and through the external wall.

19. The method of claim 15, wherein penetrating the septum comprises advancing the first guidewire through the septum and wherein penetrating the external wall comprises advancing the second guidewire through the external wall.

\* \* \* \* \*